US006200959B1

(12) United States Patent
Haynes et al.

(10) Patent No.: US 6,200,959 B1
(45) Date of Patent: *Mar. 13, 2001

(54) GENETIC INDUCTION OF ANTI-VIRAL IMMUNE RESPONSE AND GENETIC VACCINE FOR FILOVIRUS

(75) Inventors: Joel R. Haynes, Fort Collins, CO (US); Connie S. Schmaljohn, Frederick, MD (US); Deborah L. Fuller, Oregon, WI (US); Alan Schmaljohn, Frederick; Peter B. Jahrling, Middletown, both of MD (US)

(73) Assignee: PowerJect Vaccines Inc., Madison, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/760,615

(22) Filed: Dec. 4, 1996

(51) Int. Cl.[7] .......................... A61K 39/12; A61K 48/00; A61K 9/14; C12N 15/87
(52) U.S. Cl. ...................... 514/44; 424/204.1; 424/489; 435/459
(58) Field of Search ................ 514/44; 424/409, 424/204.1, 417, 489; 435/459

(56) References Cited

U.S. PATENT DOCUMENTS

| 4,945,050 | 7/1990 | Sanford et al. |
| 5,015,580 | 5/1991 | Christou et al. |
| 5,149,655 | 9/1992 | McCabe et al. |
| 5,584,807 | * 12/1996 | McCabe ................................. 604/71 |
| 5,589,466 | 12/1996 | Felgner et al. |

FOREIGN PATENT DOCUMENTS

| WO 93/17706 | 9/1993 | (WO). |
| WO 93/19183 | 9/1993 | (WO). |
| WO 95/19799 | 7/1995 | (WO). |

OTHER PUBLICATIONS

Yang et al. Nature Medicine 6(8): 886–889, Aug. 2000.*
Vaccines 97. Molecular Approaches to the Control of Infectious Diseases. Cold Spring Harbor Laboratory, Cold Spring Harbor, N.Y. pp. xix–xx, v–x, and 357–358, 1997.*
Havey, M. et al. Vaccines 97. Cold Spring Harbor Laboratory, Cold Spring Harbor, N.Y. pp. 93–98, 1997.*
Gilligan, K.J. et al. Vaccines 97. Cold Spring Harbor Laboratory, Cold Spring Harbor, N.Y. pp. 87–92, 1997.*
Pushko, P. et al. Vaccines 97. Cold Spring Harbor Laboratory, Cold Spring Harbor, N.Y. pp. 253–258, 1997.*
Liu, M.A. Annals of the New York Academy of Sciences 772: 15–20, 1995.*
Fynan et al., "DNA Vaccines: Protective Immunizations by Parenteral, Mucosal, and Gene–Gun Inoculations," *Proc. Natl.Acad. Sci.* USA 90:11478–11482 (1993).

* cited by examiner

*Primary Examiner*—Mary E. Mosher
(74) *Attorney, Agent, or Firm*—Thomas P. McCracken

(57) ABSTRACT

An approach to genetic vaccine methodology is described. A genetic construction encoding antigenic determinants of a filovirus is transfected into cells of the vaccinated individuals using a particle acceleration protocol so as to express the viral antigens in healthy cells to produce an immune response to those antigens.

11 Claims, 5 Drawing Sheets

FIG. 2

Marburg Musoke and Ravn GP DNA vaccines
ELISA titers of Hartley guinea pigs challenged with Marburg Musoke

FIG. 3

| Immunogen | Musoke GP | Ravn GP | Both GP | Both GP |
| ELISA Antigen | Musoke | Ravn | Musoke | Ravn | guinea pig number

● lived
■ died

Marburg Musoke and Ravn GP DNA vaccines
ELISA titers of Hartley guinea pigs challenged with Marburg Ravn

FIG. 4

| Immunogen | Musoke GP | Ravn GP | Both GP | Both GP |
| ELISA Antigen | Musoke | Ravn | Musoke | Ravn | guinea pig number

● lived
■ died

ELISA * with pre and post challenge sera from guinea pigs surviving Marburg challenge

*$\log_{10}$ dilution resulting in OD$\geq$0.2

◆ pre challenge
■ post challenge

FIG. 5

30 LD$_{50}$ challenge of mice immunized with Ebola GP DNA

■ 3 immunizations
◆ 2 immunizations
● Control DNA

FIG. 6

ELISA titers[a] of mice immunized 2X with Ebola GP DNA

FIG. 7

[a]Serum dilutions from 1.5 $\log_{10}$ – 3.0 $\log_{10}$ were examined

ELISA titers[a] of mice immunized 3X with Ebola GP DNA

FIG. 8

[a]Serum dilutions from 1.5 $\log_{10}$ – 3.0$_{10}$ were examined

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
        (A) LENGTH: 2172 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Ebola virus
        (B) STRAIN: Zaire (ix) FEATURE:
        (A) NAME/KEY: CDS
        (B) LOCATION: 142..2172
        (D) OTHER INFORMATION: /product= "Glycoprotein"

(xi) SEQUENCE DESCRIPTION: SEQ ID NO:1:

```
GCGATGAAGA TTAAGCCGAC AGTGAGCGTA ATCTTCATCT CTCTTAGATT ATTTGTTTTC      60

CAGAGTAGGG GTCGTCAGGT CCTTTTCAAT CGTGTAACCA AAATAAACTC CACTAGAAGG     120

ATATTGTGGG GCAACAACAC A ATG GGC GTT ACA GGA ATA TTG CAG TTA CCT      171
                         Met Gly Val Thr Gly Ile Leu Gln Leu Pro
                           1               5                  10

CGT GAT CGA TTC AAG AGG ACA TCA TTC TTT CTT TGG GTA ATT ATC CTT      219
Arg Asp Arg Phe Lys Arg Thr Ser Phe Phe Leu Trp Val Ile Ile Leu
             15                  20                  25

TTC CAA AGA ACA TTT TCC ATC CCA CTT GGA GTC ATC CAC AAT AGC ACA      267
Phe Gln Arg Thr Phe Ser Ile Pro Leu Gly Val Ile His Asn Ser Thr
         30                  35                  40

TTA CAG GTT AGT GAT GTC GAC AAA CTA GTT TGT CGT GAC AAA CTG TCA      315
Leu Gln Val Ser Asp Val Asp Lys Leu Val Cys Arg Asp Lys Leu Ser
     45                  50                  55

TCC ACA AAT CAA TTG AGA TCA GTT GGA CTG AAT CTC GAA GGG AAT GGA      363
Ser Thr Asn Gln Leu Arg Ser Val Gly Leu Asn Leu Glu Gly Asn Gly
 60                  65                  70

GTG GCA ACT GAC GTG CCA TCT GCA ACT AAA AGA TGG GGC TTC AGG TCC      411
Val Ala Thr Asp Val Pro Ser Ala Thr Lys Arg Trp Gly Phe Arg Ser
 75                  80                  85                  90

GGT GTC CCA CCA AAG GTG GTC AAT TAT GAA GCT GGT GAA TGG GCT GAA      459
Gly Val Pro Pro Lys Val Val Asn Tyr Glu Ala Gly Glu Trp Ala Glu
                 95                 100                 105

AAC TGC TAC AAT CTT GAA ATC AAA AAA CCT GAC GGG AGT GAG TGT CTA      507
Asn Cys Tyr Asn Leu Glu Ile Lys Lys Pro Asp Gly Ser Glu Cys Leu
             110                 115                 120

CCA GCA GCG CCA GAC GGG ATT CGG GGC TTC CCC CGG TGC CGG TAT GTG      555
Pro Ala Ala Pro Asp Gly Ile Arg Gly Phe Pro Arg Cys Arg Tyr Val
         125                 130                 135

CAC AAA GTA TCA GGA ACG GGA CCG TGT GCC GGA GAC TTT GCC TTC CAT      603
His Lys Val Ser Gly Thr Gly Pro Cys Ala Gly Asp Phe Ala Phe His
     140                 145                 150

AAA GAG GGT GCT TTC TTC CTG TAT GAT CGA CTT GCT TCC ACA GTT ATC      651
Lys Glu Gly Ala Phe Phe Leu Tyr Asp Arg Leu Ala Ser Thr Val Ile
155                 160                 165                 170

TAC CGA GGA ACG ACT TTC GCT GAA GGT GTC GTT GCA TTT CTG ATA CTG      699
Tyr Arg Gly Thr Thr Phe Ala Glu Gly Val Val Ala Phe Leu Ile Leu
```

```
                    175                 180                      185
CCC CAA GCT AAG AAG GAC TTC TTC AGC TCA CAC CCC TTG AGA GAG CCG       747
Pro Gln Ala Lys Lys Asp Phe Phe Ser Ser His Pro Leu Arg Glu Pro
            190                 195                 200

GTC AAT GCA ACG GAG GAC CCG TCT AGT GGC TAC TAT TCT ACC ACA ATT       795
Val Asn Ala Thr Glu Asp Pro Ser Ser Gly Tyr Tyr Ser Thr Thr Ile
            205                 210                 215

AGA TAT CAG GCT ACC GGT TTT GGA ACC AAT GAG ACA GAG TAC TTG TTC       843
Arg Tyr Gln Ala Thr Gly Phe Gly Thr Asn Glu Thr Glu Tyr Leu Phe
    220                 225                 230

GAG GTT GAC AAT TTG ACC TAC GTC CAA CTT GAA TCA AGA TTC ACA CCA       891
Glu Val Asp Asn Leu Thr Tyr Val Gln Leu Glu Ser Arg Phe Thr Pro
235                 240                 245                 250

CAG TTT CTG CTC CAG CTG AAT GAG ACA ATA TAT ACA AGT GGG AAA AGG       939
Gln Phe Leu Leu Gln Leu Asn Glu Thr Ile Tyr Thr Ser Gly Lys Arg
                255                 260                 265

AGC AAT ACC ACG GGA AAA CTA ATT TGG AAG GTC AAC CCC GAA ATT GAT       987
Ser Asn Thr Thr Gly Lys Leu Ile Trp Lys Val Asn Pro Glu Ile Asp
                270                 275                 280

ACA ACA ATC GGG GAG TGG GCC TTC TGG GAA ACT AAA AAA AAC CTC ACT      1035
Thr Thr Ile Gly Glu Trp Ala Phe Trp Glu Thr Lys Lys Asn Leu Thr
            285                 290                 295

AGA AAA ATT CGC AGT GAA GAG TTG TCT TTC ACA GTT GTA TCA AAC GGA      1083
Arg Lys Ile Arg Ser Glu Glu Leu Ser Phe Thr Val Val Ser Asn Gly
    300                 305                 310

GCC AAA AAC ATC AGT GGT CAG AGT CCG GCG CGA ACT TCT TCC GAC CCA      1131
Ala Lys Asn Ile Ser Gly Gln Ser Pro Ala Arg Thr Ser Ser Asp Pro
315                 320                 325                 330

GGG ACC AAC ACA ACA ACT GAA GAC CAC AAA ATC ATG GCT TCA GAA AAT      1179
Gly Thr Asn Thr Thr Thr Glu Asp His Lys Ile Met Ala Ser Glu Asn
                335                 340                 345

TCC TCT GCA ATG GTT CAA GTG CAC AGT CAA GGA AGG GAA GCT GCA GTG      1227
Ser Ser Ala Met Val Gln Val His Ser Gln Gly Arg Glu Ala Ala Val
                350                 355                 360

TCG CAT CTA ACA ACC CTT GCC ACA ATC TCC ACG AGT CCC CAA TCC CTC      1275
Ser His Leu Thr Thr Leu Ala Thr Ile Ser Thr Ser Pro Gln Ser Leu
            365                 370                 375

ACA ACC AAA CCA GGT CCG GAC AAC AGC ACC CAT AAT ACA CCC GTG TAT      1323
Thr Thr Lys Pro Gly Pro Asp Asn Ser Thr His Asn Thr Pro Val Tyr
    380                 385                 390

AAA CTT GAC ATC TCT GAG GCA ACT CAA GTT GAA CAA CAT CAC CGC AGA      1371
Lys Leu Asp Ile Ser Glu Ala Thr Gln Val Glu Gln His His Arg Arg
395                 400                 405                 410

ACA GAC AAC GAC AGC ACA GCC TCC GAC ACT CCC TCT GCC ACG ACC GCA      1419
Thr Asp Asn Asp Ser Thr Ala Ser Asp Thr Pro Ser Ala Thr Thr Ala
                415                 420                 425

GCC GGA CCC CCA AAA GCA GAG AAC ACC AAC ACG AGC AAG AGC ACT GAC      1467
Ala Gly Pro Pro Lys Ala Glu Asn Thr Asn Thr Ser Lys Ser Thr Asp
                430                 435                 440

TTC CTG GAC CCC GCC ACC ACA ACA AGT CCC CAA AAC CAC AGC GAG ACC      1515
Phe Leu Asp Pro Ala Thr Thr Thr Ser Pro Gln Asn His Ser Glu Thr
            445                 450                 455

GCT GGC AAC AAC AAC ACT CAT CAC CAA GAT ACC GGA GAA GAG AGT GCC      1563
Ala Gly Asn Asn Asn Thr His His Gln Asp Thr Gly Glu Glu Ser Ala
    460                 465                 470

AGC AGC GGG AAG CTA GGC TTA ATT ACC AAT ACT ATT GCT GGA GTC GCA      1611
Ser Ser Gly Lys Leu Gly Leu Ile Thr Asn Thr Ile Ala Gly Val Ala
475                 480                 485                 490

GGA CTG ATC ACA GGC GGG AGA AGA ACT CGA AGA GAA GCA ATT GTC AAT      1659
```

-continued

```
Gly Leu Ile Thr Gly Gly Arg Arg Thr Arg Arg Glu Ala Ile Val Asn
                495                 500                 505
GCT CAA CCC AAA TGC AAC CCT AAT TTA CAT TAC TGG ACT ACT CAG GAT      1707
Ala Gln Pro Lys Cys Asn Pro Asn Leu His Tyr Trp Thr Thr Gln Asp
            510                 515                 520
GAA GGT GCT GCA ATC GGA CTG GCC TGG ATA CCA TAT TTC GGG CCA GCA      1755
Glu Gly Ala Ala Ile Gly Leu Ala Trp Ile Pro Tyr Phe Gly Pro Ala
            525                 530                 535
GCC GAG GGA ATT TAC ATA GAG GGG CTA ATG CAC AAT CAA GAT GGT TTA      1803
Ala Glu Gly Ile Tyr Ile Glu Gly Leu Met His Asn Gln Asp Gly Leu
            540                 545                 550
ATC TGT GGG TTG AGA CAG CTG GCC AAC GAG ACG ACT CAA GCT CTT CAA      1851
Ile Cys Gly Leu Arg Gln Leu Ala Asn Glu Thr Thr Gln Ala Leu Gln
555                 560                 565                 570
CTG TTC CTG AGA GCC ACA ACT GAG CTA CGC ACC TTT TCA ATC CTC AAC      1899
Leu Phe Leu Arg Ala Thr Thr Glu Leu Arg Thr Phe Ser Ile Leu Asn
                575                 580                 585
CGT AAG GCA ATT GAT TTC TTG CTG CAG CGA TGG GGC GGC ACA TGC CAC      1947
Arg Lys Ala Ile Asp Phe Leu Leu Gln Arg Trp Gly Gly Thr Cys His
                590                 595                 600
ATT CTG GGA CCG GAC TGC TGT ATC GAA CCA CAT GAT TGG ACC AAG AAC      1995
Ile Leu Gly Pro Asp Cys Cys Ile Glu Pro His Asp Trp Thr Lys Asn
                605                 610                 615
ATA ACA GAC AAA ATT GAT CAG ATT ATT CAT GAT TTT GTT GAT AAA ACC      2043
Ile Thr Asp Lys Ile Asp Gln Ile Ile His Asp Phe Val Asp Lys Thr
            620                 625                 630
CTT CCG GAC CAG GGG GAC AAT GAC AAT TGG TGG ACA GGA TGG AGA CAA      2091
Leu Pro Asp Gln Gly Asp Asn Asp Asn Trp Trp Thr Gly Trp Arg Gln
635                 640                 645                 650
TGG ATA CCG GCA GGT ATT GGA GTT ACA GGC GTT ATA ATT GCA GTT ATC      2139
Trp Ile Pro Ala Gly Ile Gly Val Thr Gly Val Ile Ile Ala Val Ile
                655                 660                 665
GCT TTA TTC TGT ATA TGC AAA TTT GTC TTT TAG                          2172
Ala Leu Phe Cys Ile Cys Lys Phe Val Phe  *
            670                 675
```

(2) INFORMATION FOR SEQ ID NO:2:

(i) SEQUENCE CHARACTERISTICS:
        (A) LENGTH: 676 amino acids
        (B) TYPE: amino acid
        (D) TOPOLOGY: linear (ii) MOLECULE TYPE: protein (xi) SEQUENCE DESCRIPTION: SEQ ID NO:2:

```
Met Gly Val Thr Gly Ile Leu Gln Leu Pro Arg Asp Arg Phe Lys Arg
 1               5                  10                  15

Thr Ser Phe Phe Leu Trp Val Ile Ile Leu Phe Gln Arg Thr Phe Ser
                20                  25                  30

Ile Pro Leu Gly Val Ile His Asn Ser Thr Leu Gln Val Ser Asp Val
            35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
                100                 105                 110
```

-continued

```
Ile Lys Lys Pro Asp Gly Ser Glu Cys Leu Pro Ala Ala Pro Asp Gly
        115                 120                 125
Ile Arg Gly Phe Pro Arg Cys Arg Tyr Val His Lys Val Ser Gly Thr
        130                 135                 140
Gly Pro Cys Ala Gly Asp Phe Ala Phe His Lys Glu Gly Ala Phe Phe
145                 150                 155                 160
Leu Tyr Asp Arg Leu Ala Ser Thr Val Ile Tyr Arg Gly Thr Thr Phe
                165                 170                 175
Ala Glu Gly Val Val Ala Phe Leu Ile Leu Pro Gln Ala Lys Lys Asp
                180                 185                 190
Phe Phe Ser Ser His Pro Leu Arg Glu Pro Val Asn Ala Thr Glu Asp
                195                 200                 205
Pro Ser Ser Gly Tyr Tyr Ser Thr Thr Ile Arg Tyr Gln Ala Thr Gly
        210                 215                 220
Phe Gly Thr Asn Glu Thr Glu Tyr Leu Phe Glu Val Asp Asn Leu Thr
225                 230                 235                 240
Tyr Val Gln Leu Glu Ser Arg Phe Thr Pro Gln Phe Leu Leu Gln Leu
                245                 250                 255
Asn Glu Thr Ile Tyr Thr Ser Gly Lys Arg Ser Asn Thr Thr Gly Lys
                260                 265                 270
Leu Ile Trp Lys Val Asn Pro Glu Ile Asp Thr Thr Ile Gly Glu Trp
        275                 280                 285
Ala Phe Trp Glu Thr Lys Lys Asn Leu Thr Arg Lys Ile Arg Ser Glu
        290                 295                 300
Glu Leu Ser Phe Thr Val Val Ser Asn Gly Ala Lys Asn Ile Ser Gly
305                 310                 315                 320
Gln Ser Pro Ala Arg Thr Ser Ser Asp Pro Gly Thr Asn Thr Thr Thr
                325                 330                 335
Glu Asp His Lys Ile Met Ala Ser Glu Asn Ser Ser Ala Met Val Gln
                340                 345                 350
Val His Ser Gln Gly Arg Glu Ala Ala Val Ser His Leu Thr Thr Leu
        355                 360                 365
Ala Thr Ile Ser Thr Ser Pro Gln Ser Leu Thr Thr Lys Pro Gly Pro
        370                 375                 380
Asp Asn Ser Thr His Asn Thr Pro Val Tyr Lys Leu Asp Ile Ser Glu
385                 390                 395                 400
Ala Thr Gln Val Glu Gln His Arg Arg Thr Asp Asn Asp Ser Thr
                405                 410                 415
Ala Ser Asp Thr Pro Ser Ala Thr Thr Ala Ala Gly Pro Pro Lys Ala
                420                 425                 430
Glu Asn Thr Asn Thr Ser Lys Ser Thr Asp Phe Leu Asp Pro Ala Thr
        435                 440                 445
Thr Thr Ser Pro Gln Asn His Ser Glu Thr Ala Gly Asn Asn Asn Thr
        450                 455                 460
His His Gln Asp Thr Gly Glu Glu Ser Ala Ser Ser Gly Lys Leu Gly
465                 470                 475                 480
Leu Ile Thr Asn Thr Ile Ala Gly Val Ala Gly Leu Ile Thr Gly Gly
                485                 490                 495
Arg Arg Thr Arg Arg Glu Ala Ile Val Asn Ala Gln Pro Lys Cys Asn
                500                 505                 510
Pro Asn Leu His Tyr Trp Thr Thr Gln Asp Glu Gly Ala Ala Ile Gly
        515                 520                 525
```

```
Leu Ala Trp Ile Pro Tyr Phe Gly Pro Ala Ala Glu Gly Ile Tyr Ile
    530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
                580                 585                 590

Leu Leu Gln Arg Trp Gly Gly Thr Cys His Ile Leu Gly Pro Asp Cys
                595                 600                 605

Cys Ile Glu Pro His Asp Trp Thr Lys Asn Ile Thr Asp Lys Ile Asp
            610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                    645                 650                 655

Gly Val Thr Gly Val Ile Ile Ala Val Ile Ala Leu Phe Cys Ile Cys
                660                 665                 670

Lys Phe Val Phe
    675
```

(2) INFORMATION FOR SEQ ID NO:3:

(i) SEQUENCE CHARACTERISTICS:
        (A) LENGTH: 2164 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Marburg virus
        (B) STRAIN: Musoke (ix) FEATURE:
        (A) NAME/KEY: CDS
        (B) LOCATION: 119..2164

(xi) SEQUENCE DESCRIPTION: SEQ ID NO:3:

```
ATGAAGAACA TTAATTGCTG GGTAAAAGTG ATTAATTTCT TTAAATTTGA CCAGAATAAT      60

ATTTTGTCAG TGAATATATT CTCATATCAC TTGATTAAAA ACAGAAAATT ACCCTAAC      118

ATG AAG ACC ACA TGT TTC CTT ATC AGT CTT ATC TTA ATT CAA GGG ACA      166
Met Lys Thr Thr Cys Phe Leu Ile Ser Leu Ile Leu Ile Gln Gly Thr
    680                 685                 690

AAA AAT CTC CCC ATT TTA GAG ATA GCT AGT AAT AAT CAA CCC CAA AAT      214
Lys Asn Leu Pro Ile Leu Glu Ile Ala Ser Asn Asn Gln Pro Gln Asn
    695                 700                 705

GTG GAT TCG GTA TGC TCC GGA ACT CTC CAG AAG ACA GAA GAC GTC CAT      262
Val Asp Ser Val Cys Ser Gly Thr Leu Gln Lys Thr Glu Asp Val His
710                 715                 720                 725

CTG ATG GGA TTC ACA CTG AGT GGG CAA AAA GTT GCT GAT TCC CCT TTG      310
Leu Met Gly Phe Thr Leu Ser Gly Gln Lys Val Ala Asp Ser Pro Leu
                730                 735                 740

GAG GCA TCC AAG CGA TGG GCT TTC AGG ACA GGT GTA CCT CCC AAG AAT      358
Glu Ala Ser Lys Arg Trp Ala Phe Arg Thr Gly Val Pro Pro Lys Asn
                745                 750                 755

GTT GAG TAC ACA GAG GGG GAG GAA GCC AAA ACA TGC TAC AAT ATA AGT      406
Val Glu Tyr Thr Glu Gly Glu Glu Ala Lys Thr Cys Tyr Asn Ile Ser
                760                 765                 770
```

```
                                                        -continued

GTA ACG GAT CCC TCT GGA AAA TCC TTG CTG TTA GAT CCT CCT ACC AAC    454
Val Thr Asp Pro Ser Gly Lys Ser Leu Leu Leu Asp Pro Pro Thr Asn
        775                 780                 785

ATC CGT GAC TAT CCT AAA TGC AAA ACT ATC CAT CAT ATT CAA GGT CAA    502
Ile Arg Asp Tyr Pro Lys Cys Lys Thr Ile His His Ile Gln Gly Gln
790                 795                 800                 805

AAC CCT CAT GCA CAG GGG ATC GCC CTT CAT TTA TGG GGA GCA TTT TTT    550
Asn Pro His Ala Gln Gly Ile Ala Leu His Leu Trp Gly Ala Phe Phe
                810                 815                 820

CTG TAT GAT CGC ATT GCC TCC ACA ACA ATG TAC CGA GGC AAA GTC TTC    598
Leu Tyr Asp Arg Ile Ala Ser Thr Thr Met Tyr Arg Gly Lys Val Phe
        825                 830                 835

ACT GAA GGG AAC ATA GCA GCT ATG ATT GTC AAT AAG ACA GTG CAC AAA    646
Thr Glu Gly Asn Ile Ala Ala Met Ile Val Asn Lys Thr Val His Lys
        840                 845                 850

ATG ATT TTC TCG CGG CAA GGA CAA GGG TAC CGT CAT ATG AAT CTG ACT    694
Met Ile Phe Ser Arg Gln Gly Gln Gly Tyr Arg His Met Asn Leu Thr
        855                 860                 865

TCT ACT AAT AAA TAT TGG ACA AGT AGT AAC GGA ACG CAA ACG AAT GAC    742
Ser Thr Asn Lys Tyr Trp Thr Ser Ser Asn Gly Thr Gln Thr Asn Asp
870                 875                 880                 885

ACT GGA TGT TTC GGC GCT CTT CAA GAA TAC AAT TCT ACA AAG AAC CAA    790
Thr Gly Cys Phe Gly Ala Leu Gln Glu Tyr Asn Ser Thr Lys Asn Gln
                890                 895                 900

ACA TGT GCT CCG TCC AAA ATA CCT CCA CCA CTG CCC ACA GCC CGT CCG    838
Thr Cys Ala Pro Ser Lys Ile Pro Pro Pro Leu Pro Thr Ala Arg Pro
                905                 910                 915

GAG ATC AAA CTC ACA AGC ACC CCA ACT GAT GCC ACC AAA CTC AAT ACC    886
Glu Ile Lys Leu Thr Ser Thr Pro Thr Asp Ala Thr Lys Leu Asn Thr
        920                 925                 930

ACG GAC CCA AGC AGT GAT GAT GAG GAC CTC GCA ACA TCC GGC TCA GGG    934
Thr Asp Pro Ser Ser Asp Asp Glu Asp Leu Ala Thr Ser Gly Ser Gly
935                 940                 945

TCC GGA GAA CGA GAA CCC CAC ACA ACT TCT GAT GCG GTC ACC AAG CAA    982
Ser Gly Glu Arg Glu Pro His Thr Thr Ser Asp Ala Val Thr Lys Gln
950                 955                 960                 965

GGG CTT TCA TCA ACA ATG CCA CCC ACT CCC TCA CCA CAA CCA AGC ACG    1030
Gly Leu Ser Ser Thr Met Pro Pro Thr Pro Ser Pro Gln Pro Ser Thr
                970                 975                 980

CCA CAG CAA GGA GGA AAC AAC ACA AAC CAT TCC CAA GAT GCT GTG ACT    1078
Pro Gln Gln Gly Gly Asn Asn Thr Asn His Ser Gln Asp Ala Val Thr
                985                 990                 995

GAA CTA GAC AAA AAT AAC ACA ACT GCA CAA CCG TCC ATG CCC CCT CAT    1126
Glu Leu Asp Lys Asn Asn Thr Thr Ala Gln Pro Ser Met Pro Pro His
                1000                1005                1010

AAC ACT ACC ACA ATC TCT ACT AAC AAC ACC TCC AAA CAC AAC TTC AGC    1174
Asn Thr Thr Thr Ile Ser Thr Asn Asn Thr Ser Lys His Asn Phe Ser
        1015                1020                1025

ACT CTC TCT GCA CCA TTA CAA AAC ACC ACC AAT GAC AAC ACA CAG AGC    1222
Thr Leu Ser Ala Pro Leu Gln Asn Thr Thr Asn Asp Asn Thr Gln Ser
1030                1035                1040                1045

ACA ATC ACT GAA AAT GAG CAA ACC AGT GCC CCC TCG ATA ACA ACC CTG    1270
Thr Ile Thr Glu Asn Glu Gln Thr Ser Ala Pro Ser Ile Thr Thr Leu
                1050                1055                1060

CCT CCA ACG GGA AAT CCC ACC ACA GCA AAG AGC ACC AGC AGC AAA AAA    1318
Pro Pro Thr Gly Asn Pro Thr Thr Ala Lys Ser Thr Ser Ser Lys Lys
                1065                1070                1075

GGC CCC GCC ACA ACG GCA CCA AAC ACG ACA AAT GAG CAT TTC ACC AGT    1366
Gly Pro Ala Thr Thr Ala Pro Asn Thr Thr Asn Glu His Phe Thr Ser
        1080                1085                1090
```

```
CCT CCC CCC ACC CCC AGC TCG ACT GCA CAA CAT CTT GTA TAT TTC AGA      1414
Pro Pro Pro Thr Pro Ser Ser Thr Ala Gln His Leu Val Tyr Phe Arg
        1095                1100                1105

AGA AAG CGA AGT ATC CTC TGG AGG GAA GGC GAC ATG TTC CCT TTT CTG      1462
Arg Lys Arg Ser Ile Leu Trp Arg Glu Gly Asp Met Phe Pro Phe Leu
1110            1115                1120                1125

GAT GGG TTA ATA AAT GCT CCA ATT GAT TTT GAC CCA GTT CCA AAT ACA      1510
Asp Gly Leu Ile Asn Ala Pro Ile Asp Phe Asp Pro Val Pro Asn Thr
                1130                1135                1140

AAA ACA ATC TTT GAT GAA TCC TCT AGT TCT GGT GCC TCG GCT GAG GAA      1558
Lys Thr Ile Phe Asp Glu Ser Ser Ser Ser Gly Ala Ser Ala Glu Glu
            1145                1150                1155

GAT CAA CAT GCC TCC CCC AAT ATT AGT TTA ACT TTA TCT TAT TTT CCT      1606
Asp Gln His Ala Ser Pro Asn Ile Ser Leu Thr Leu Ser Tyr Phe Pro
        1160                1165                1170

AAT ATA AAT GAG AAC ACT GCC TAC TCT GGA GAA AAT GAG AAT GAT TGT      1654
Asn Ile Asn Glu Asn Thr Ala Tyr Ser Gly Glu Asn Glu Asn Asp Cys
    1175                1180                1185

GAT GCA GAG TTA AGA ATT TGG AGC GTT CAG GAG GAT GAC CTG GCC GCA      1702
Asp Ala Glu Leu Arg Ile Trp Ser Val Gln Glu Asp Asp Leu Ala Ala
1190            1195                1200                1205

GGG CTC AGT TGG ATA CCG TTT TTT GGC CCT GGA ATT GAA GGA CTT TAC      1750
Gly Leu Ser Trp Ile Pro Phe Phe Gly Pro Gly Ile Glu Gly Leu Tyr
                1210                1215                1220

ACT GCT GTT TTA ATT AAA AAT CAA AAC AAT TTG GTC TGC AGG TTG AGG      1798
Thr Ala Val Leu Ile Lys Asn Gln Asn Asn Leu Val Cys Arg Leu Arg
            1225                1230                1235

CGT CTA GCC AAT CAA ACT GCC AAA TCC TTG GAA CTC TTA TTG AGA GTC      1846
Arg Leu Ala Asn Gln Thr Ala Lys Ser Leu Glu Leu Leu Leu Arg Val
        1240                1245                1250

ACA ACT GAG GAA AGA ACA TTC TCC TTA ATC AAT AGA CAT GCT ATT GAC      1894
Thr Thr Glu Glu Arg Thr Phe Ser Leu Ile Asn Arg His Ala Ile Asp
    1255                1260                1265

TTT CTA CTC ACA AGA TGG GGA GGA ACA TGC AAA GTG CTT GGA CCT GAT      1942
Phe Leu Leu Thr Arg Trp Gly Gly Thr Cys Lys Val Leu Gly Pro Asp
1270            1275                1280                1285

TGT TGC ATC GGG ATA GAA GAC TTG TCC AAA AAT ATT TCA GAG CAA ATT      1990
Cys Cys Ile Gly Ile Glu Asp Leu Ser Lys Asn Ile Ser Glu Gln Ile
                1290                1295                1300

GAC CAA ATT AAA AAG GAC GAA CAA AAA GAG GGG ACT GGT TGG GGT CTG      2038
Asp Gln Ile Lys Lys Asp Glu Gln Lys Glu Gly Thr Gly Trp Gly Leu
            1305                1310                1315

GGT GGT AAA TGG TGG ACA TCC GAC TGG GGT GTT CTT ACT AAC TTG GGC      2086
Gly Gly Lys Trp Trp Thr Ser Asp Trp Gly Val Leu Thr Asn Leu Gly
        1320                1325                1330

ATT TTG CTA CTA TTA TCC ATA GCT GTC TTG ATT GCT CTA TCC TGT ATT      2134
Ile Leu Leu Leu Leu Ser Ile Ala Val Leu Ile Ala Leu Ser Cys Ile
    1335                1340                1345

TGT CGT ATC TTT ACT AAA TAT ATC GGA TAA                              2164
Cys Arg Ile Phe Thr Lys Tyr Ile Gly *
1350            1355
```

(2) INFORMATION FOR SEQ ID NO:4:

(i) SEQUENCE CHARACTERISTICS:
        (A) LENGTH: 681 amino acids
        (B) TYPE: amino acid
        (D) TOPOLOGY: linear (ii) MOLECULE TYPE: protein -continued (xi) SEQUENCE DESCRIPTION: SEQ ID NO:4:

| Met | Lys | Thr | Thr | Cys | Phe | Leu | Ile | Ser | Leu | Ile | Leu | Ile | Gln | Gly | Thr |
|---|---|---|---|---|---|---|---|---|---|---|---|---|---|---|---|
| 1 | | | | 5 | | | | | 10 | | | | | 15 | |

| Lys | Asn | Leu | Pro | Ile | Leu | Glu | Ile | Ala | Ser | Asn | Asn | Gln | Pro | Gln | Asn |
| | | | 20 | | | | | 25 | | | | | 30 | | |

| Val | Asp | Ser | Val | Cys | Ser | Gly | Thr | Leu | Gln | Lys | Thr | Glu | Asp | Val | His |
| | | 35 | | | | | 40 | | | | | 45 | | | |

| Leu | Met | Gly | Phe | Thr | Leu | Ser | Gly | Gln | Lys | Val | Ala | Asp | Ser | Pro | Leu |
| | 50 | | | | | 55 | | | | | 60 | | | | |

| Glu | Ala | Ser | Lys | Arg | Trp | Ala | Phe | Arg | Thr | Gly | Val | Pro | Pro | Lys | Asn |
| 65 | | | | | 70 | | | | | 75 | | | | | 80 |

| Val | Glu | Tyr | Thr | Glu | Gly | Glu | Ala | Lys | Thr | Cys | Tyr | Asn | Ile | Ser |
| | | | | 85 | | | | | 90 | | | | | 95 |

| Val | Thr | Asp | Pro | Ser | Gly | Lys | Ser | Leu | Leu | Leu | Asp | Pro | Pro | Thr | Asn |
| | | | | 100 | | | | | 105 | | | | | 110 | |

| Ile | Arg | Asp | Tyr | Pro | Lys | Cys | Lys | Thr | Ile | His | His | Ile | Gln | Gly | Gln |
| | | | 115 | | | | | 120 | | | | | 125 | | |

| Asn | Pro | His | Ala | Gln | Gly | Ile | Ala | Leu | His | Leu | Trp | Gly | Ala | Phe | Phe |
| | | 130 | | | | | 135 | | | | | 140 | | | |

| Leu | Tyr | Asp | Arg | Ile | Ala | Ser | Thr | Thr | Met | Tyr | Arg | Gly | Lys | Val | Phe |
| 145 | | | | | 150 | | | | | 155 | | | | | 160 |

| Thr | Glu | Gly | Asn | Ile | Ala | Ala | Met | Ile | Val | Asn | Lys | Thr | Val | His | Lys |
| | | | | 165 | | | | | 170 | | | | | 175 | |

| Met | Ile | Phe | Ser | Arg | Gln | Gly | Gln | Gly | Tyr | Arg | His | Met | Asn | Leu | Thr |
| | | | | 180 | | | | | 185 | | | | | 190 | |

| Ser | Thr | Asn | Lys | Tyr | Trp | Thr | Ser | Ser | Asn | Gly | Thr | Gln | Thr | Asn | Asp |
| | | | 195 | | | | | 200 | | | | | 205 | | |

| Thr | Gly | Cys | Phe | Gly | Ala | Leu | Gln | Glu | Tyr | Asn | Ser | Thr | Lys | Asn | Gln |
| | | 210 | | | | | 215 | | | | | 220 | | | |

| Thr | Cys | Ala | Pro | Ser | Lys | Ile | Pro | Pro | Leu | Pro | Thr | Ala | Arg | Pro |
| 225 | | | | | 230 | | | | | 235 | | | | | 240 |

| Glu | Ile | Lys | Leu | Thr | Ser | Thr | Pro | Thr | Asp | Ala | Thr | Lys | Leu | Asn | Thr |
| | | | | 245 | | | | | 250 | | | | | 255 | |

| Thr | Asp | Pro | Ser | Ser | Asp | Asp | Glu | Asp | Leu | Ala | Thr | Ser | Gly | Ser | Gly |
| | | | 260 | | | | | 265 | | | | | 270 | | |

| Ser | Gly | Glu | Arg | Glu | Pro | His | Thr | Thr | Ser | Asp | Ala | Val | Thr | Lys | Gln |
| | | | 275 | | | | | 280 | | | | | 285 | | |

| Gly | Leu | Ser | Ser | Thr | Met | Pro | Pro | Thr | Pro | Ser | Gln | Pro | Ser | Thr |
| | 290 | | | | | 295 | | | | | 300 | | | | |

| Pro | Gln | Gln | Gly | Gly | Asn | Asn | Thr | Asn | His | Ser | Gln | Asp | Ala | Val | Thr |
| 305 | | | | | 310 | | | | | 315 | | | | | 320 |

| Glu | Leu | Asp | Lys | Asn | Asn | Thr | Thr | Ala | Gln | Pro | Ser | Met | Pro | Pro | His |
| | | | | 325 | | | | | 330 | | | | | 335 | |

| Asn | Thr | Thr | Thr | Ile | Ser | Thr | Asn | Asn | Thr | Ser | Lys | His | Asn | Phe | Ser |
| | | | 340 | | | | | 345 | | | | | 350 | | |

| Thr | Leu | Ser | Ala | Pro | Leu | Gln | Asn | Thr | Thr | Asn | Asp | Asn | Thr | Gln | Ser |
| | | | 355 | | | | | 360 | | | | | 365 | | |

| Thr | Ile | Thr | Glu | Asn | Glu | Gln | Thr | Ser | Ala | Pro | Ser | Ile | Thr | Thr | Leu |
| | | 370 | | | | | 375 | | | | | 380 | | | |

| Pro | Pro | Thr | Gly | Asn | Pro | Thr | Thr | Ala | Lys | Ser | Thr | Ser | Ser | Lys | Lys |
| 385 | | | | | 390 | | | | | 395 | | | | | 400 |

| Gly | Pro | Ala | Thr | Thr | Ala | Pro | Asn | Thr | Thr | Asn | Glu | His | Phe | Thr | Ser |
| | | | | 405 | | | | | 410 | | | | | 415 | |

```
Pro Pro Pro Thr Pro Ser Ser Thr Ala Gln His Leu Val Tyr Phe Arg
            420                 425                 430

Arg Lys Arg Ser Ile Leu Trp Arg Glu Gly Asp Met Phe Pro Phe Leu
        435                 440                 445

Asp Gly Leu Ile Asn Ala Pro Ile Asp Phe Asp Pro Val Pro Asn Thr
    450                 455                 460

Lys Thr Ile Phe Asp Glu Ser Ser Ser Gly Ala Ser Ala Glu Glu
465                 470                 475                 480

Asp Gln His Ala Ser Pro Asn Ile Ser Leu Thr Leu Ser Tyr Phe Pro
                485                 490                 495

Asn Ile Asn Glu Asn Thr Ala Tyr Ser Gly Glu Asn Glu Asn Asp Cys
            500                 505                 510

Asp Ala Glu Leu Arg Ile Trp Ser Val Gln Glu Asp Asp Leu Ala Ala
        515                 520                 525

Gly Leu Ser Trp Ile Pro Phe Phe Gly Pro Gly Ile Glu Gly Leu Tyr
    530                 535                 540

Thr Ala Val Leu Ile Lys Asn Gln Asn Asn Leu Val Cys Arg Leu Arg
545                 550                 555                 560

Arg Leu Ala Asn Gln Thr Ala Lys Ser Leu Glu Leu Leu Arg Val
                565                 570                 575

Thr Thr Glu Glu Arg Thr Phe Ser Leu Ile Asn Arg His Ala Ile Asp
            580                 585                 590

Phe Leu Leu Thr Arg Trp Gly Gly Thr Cys Lys Val Leu Gly Pro Asp
        595                 600                 605

Cys Cys Ile Gly Ile Glu Asp Leu Ser Lys Asn Ile Ser Glu Gln Ile
    610                 615                 620

Asp Gln Ile Lys Lys Asp Glu Gln Lys Glu Gly Thr Gly Trp Gly Leu
625                 630                 635                 640

Gly Gly Lys Trp Trp Thr Ser Asp Trp Gly Val Leu Thr Asn Leu Gly
                645                 650                 655

Ile Leu Leu Leu Leu Ser Ile Ala Val Leu Ile Ala Leu Ser Cys Ile
            660                 665                 670

Cys Arg Ile Phe Thr Lys Tyr Ile Gly
        675                 680

(2) INFORMATION FOR SEQ ID NO:5:

(i) SEQUENCE CHARACTERISTICS:
        (A) LENGTH: 2247 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Marburg virus
        (B) STRAIN: Ravn (ix) FEATURE:
        (A) NAME/KEY: CDS
        (B) LOCATION: 97..2142

(xi) SEQUENCE DESCRIPTION: SEQ ID NO:5:

GCAGGCAATT AAGTTCTTTG AACTTTGCAA AGTAAGGGT TTCACTAGTG AGTAAATTCC      60

TGTATTAGTA GATTAAAACC AAGGAAGCAC CCCGAC ATG AAG ACC ATA TAT TTT     114
                                        Met Lys Thr Ile Tyr Phe
                                        685
```

```
CTG ATT AGT CTC ATT TTA ATC CAA AGT ATA AAA ACT CTC CCT GTT TTA    162
Leu Ile Ser Leu Ile Leu Ile Gln Ser Ile Lys Thr Leu Pro Val Leu
        690             695             700

GAA ATT GCT AGT AAC AGC CAA CCT CAA GAT GTA GAT TCA GTG TGC TCC    210
Glu Ile Ala Ser Asn Ser Gln Pro Gln Asp Val Asp Ser Val Cys Ser
705             710             715                 720

GGA ACC CTC CAA AAG ACA GAA GAT GTT CAT CTG ATG GGA TTT ACA CTG    258
Gly Thr Leu Gln Lys Thr Glu Asp Val His Leu Met Gly Phe Thr Leu
            725             730             735

AGT GGG CAA AAA GTT GCT GAT TCC CCT TTG GAA GCA TCT AAA CGA TGG    306
Ser Gly Gln Lys Val Ala Asp Ser Pro Leu Glu Ala Ser Lys Arg Trp
        740             745             750

GCT TTC AGG ACA GGT GTT CCT CCC AAG AAC GTT GAG TAT ACG GAA GGA    354
Ala Phe Arg Thr Gly Val Pro Pro Lys Asn Val Glu Tyr Thr Glu Gly
            755             760             765

GAA GAA GCC AAA ACA TGT TAC AAT ATA AGT GTA ACA GAC CCT TCT GGA    402
Glu Glu Ala Lys Thr Cys Tyr Asn Ile Ser Val Thr Asp Pro Ser Gly
770             775             780

AAA TCC TTG CTG CTG GAT CCT CCC AGT AAT ATC CGC GAT TAC CCT AAA    450
Lys Ser Leu Leu Leu Asp Pro Pro Ser Asn Ile Arg Asp Tyr Pro Lys
785             790             795             800

TGT AAA ACT GTT CAT CAT ATT CAA GGT CAA AAC CCT CAT GCA CAG GGG    498
Cys Lys Thr Val His His Ile Gln Gly Gln Asn Pro His Ala Gln Gly
            805             810             815

ATT GCC CTC CAT TTG TGG GGG GCA TTT TTC TTG TAT GAT CGC GTT GCC    546
Ile Ala Leu His Leu Trp Gly Ala Phe Phe Leu Tyr Asp Arg Val Ala
        820             825             830

TCT ACA ACA ATG TAC CGA GGC AAG GTC TTC ACT GAA GGA AAT ATA GCA    594
Ser Thr Thr Met Tyr Arg Gly Lys Val Phe Thr Glu Gly Asn Ile Ala
            835             840             845

GCT ATG ATT GTT AAT AAG ACA GTT CAC AGA ATG ATT TTT TCT AGG CAA    642
Ala Met Ile Val Asn Lys Thr Val His Arg Met Ile Phe Ser Arg Gln
850             855             860

GGA CAA GGT TAT CGT CAC ATG AAC TTG ACC TCC ACC AAT AAA TAT TGG    690
Gly Gln Gly Tyr Arg His Met Asn Leu Thr Ser Thr Asn Lys Tyr Trp
865             870             875             880

ACA AGC AGC AAT GAA ACG CAG AGA AAT GAT ACG GGA TGT TTT GGC ATC    738
Thr Ser Ser Asn Glu Thr Gln Arg Asn Asp Thr Gly Cys Phe Gly Ile
            885             890             895

CTC CAA GAA TAC AAC TCC ACA AAC AAT CAA ACA TGC CCT CCA TCT CTT    786
Leu Gln Glu Tyr Asn Ser Thr Asn Asn Gln Thr Cys Pro Pro Ser Leu
        900             905             910

AAA CCT CCA TCC CTG CCC ACA GTA ACT CCG AGC ATT CAC TCT ACA AAT    834
Lys Pro Pro Ser Leu Pro Thr Val Thr Pro Ser Ile His Ser Thr Asn
            915             920             925

ACT CAA ATT AAT ACT GCT AAA TCT GGA ACT ATG AAC CCA AGT AGC GAC    882
Thr Gln Ile Asn Thr Ala Lys Ser Gly Thr Met Asn Pro Ser Ser Asp
        930             935             940

GAT GAG GAC CTT ATG ATT TCC GGC TCA GGA TCT GGA GAA CAG GGG CCC    930
Asp Glu Asp Leu Met Ile Ser Gly Ser Gly Ser Gly Glu Gln Gly Pro
945             950             955             960

CAC ACA ACT CTT AAT GTA GTC ACT GAA CAG AAA CAA TCG TCA ACA ATA    978
His Thr Thr Leu Asn Val Val Thr Glu Gln Lys Gln Ser Ser Thr Ile
            965             970             975

TTG TCC ACT CCT TCA CTA CAT CCA AGC ACC TCA CAA CAT GAG CAA AAC    1026
Leu Ser Thr Pro Ser Leu His Pro Ser Thr Ser Gln His Glu Gln Asn
        980             985             990

AGT ACG AAT CCT TCC CGA CAT GCT GTA ACT GAG CAC AAT GGA ACC GAC    1074
Ser Thr Asn Pro Ser Arg His Ala Val Thr Glu His Asn Gly Thr Asp
            995             1000            1005
```

```
CCA ACA ACA CAA CCA GCA ACG CTC CTC AAC AAT ACT AAT ACA ACT CCC    1122
Pro Thr Thr Gln Pro Ala Thr Leu Leu Asn Asn Thr Asn Thr Thr Pro
        1010                1015                1020

ACC TAT AAC ACT CTC AAG TAC AAC CTC AGT ACT CCT TCC CCT CCA ACC    1170
Thr Tyr Asn Thr Leu Lys Tyr Asn Leu Ser Thr Pro Ser Pro Pro Thr
1025                1030                1035                1040

CGC AAC ATC ACC AAT AAT GAT ACA CAA CGT GCA ACT AGC AGA AAG CGA    1218
Arg Asn Ile Thr Asn Asn Asp Thr Gln Arg Ala Thr Ser Arg Lys Arg
                1045                1050                1055

CAA ACC AAT GCT CAG TTG AAC ACA ACT CTA GAT CCA ACA GAA AAT CCC    1266
Gln Thr Asn Ala Gln Leu Asn Thr Thr Leu Asp Pro Thr Glu Asn Pro
        1060                1065                1070

ACC ACA GGA CAA GAC ACC AAC AGC ACA ACC AAC ATC ATC ATG ACG ACA    1314
Thr Thr Gly Gln Asp Thr Asn Ser Thr Thr Asn Ile Ile Met Thr Thr
        1075                1080                1085

TCA GAT ATA ACA AGC AAA CAC CCC ACA AAT TCT TCT CCG GAT TCT AGT    1362
Ser Asp Ile Thr Ser Lys His Pro Thr Asn Ser Ser Pro Asp Ser Ser
        1090                1095                1100

CCG ACA ACC CGC CCT CCT ATA TAC TTT AGA AAG AAA CGA AGC ATT TTC    1410
Pro Thr Thr Arg Pro Pro Ile Tyr Phe Arg Lys Lys Arg Ser Ile Phe
1105                1110                1115                1120

TGG AAA GAA GGT GAT ATA TTC CCG TTT TTA GAT GGG TTA ATA AAT ACT    1458
Trp Lys Glu Gly Asp Ile Phe Pro Phe Leu Asp Gly Leu Ile Asn Thr
                1125                1130                1135

GAA ATT GAT TTT GAT CCA ATC CCA AAC ACA GAA ACA ATC TTT GAT GAA    1506
Glu Ile Asp Phe Asp Pro Ile Pro Asn Thr Glu Thr Ile Phe Asp Glu
        1140                1145                1150

TCT CCC AGC TTT AAT ACT TCA ACT AAT GAG GAA CAA CAC ACT CCC CCG    1554
Ser Pro Ser Phe Asn Thr Ser Thr Asn Glu Glu Gln His Thr Pro Pro
        1155                1160                1165

AAT ATC AGT TTA ACT TTC TCT TAT TTT CCT GAT AAA AAT GGA GAT ACT    1602
Asn Ile Ser Leu Thr Phe Ser Tyr Phe Pro Asp Lys Asn Gly Asp Thr
        1170                1175                1180

GCC TAC TCT GGG GAA AAC GAG AAT GAT TGT GAT GCA GAG TTG AGG ATT    1650
Ala Tyr Ser Gly Glu Asn Glu Asn Asp Cys Asp Ala Glu Leu Arg Ile
1185                1190                1195                1200

TGG AGT GTG CAG GAG GAC GAT TTG GCG GCA GGG CTT AGC TGG ATA CCA    1698
Trp Ser Val Gln Glu Asp Asp Leu Ala Ala Gly Leu Ser Trp Ile Pro
                1205                1210                1215

TTT TTT GGC CCT GGA ATC GAA GGA CTC TAT ACT GCC GGT TTA ATC AAA    1746
Phe Phe Gly Pro Gly Ile Glu Gly Leu Tyr Thr Ala Gly Leu Ile Lys
        1220                1225                1230

AAT CAG AAC AAT TTA GTT TGT AGG TTG AGG CGC TTA GCT AAT CAA ACT    1794
Asn Gln Asn Asn Leu Val Cys Arg Leu Arg Arg Leu Ala Asn Gln Thr
        1235                1240                1245

GCT AAA TCC TTG GAG CTC TTG TTA AGG GTC ACA ACC GAG GAA AGG ACA    1842
Ala Lys Ser Leu Glu Leu Leu Leu Arg Val Thr Thr Glu Glu Arg Thr
        1250                1255                1260

TTT TCC TTA ATC AAT AGG CAT GCA ATT GAC TTT TTG CTT ACG AGG TGG    1890
Phe Ser Leu Ile Asn Arg His Ala Ile Asp Phe Leu Leu Thr Arg Trp
1265                1270                1275                1280

GGC GGA ACA TGC AAG GTG CTA GGA CCT GAT TGT TGC ATA GGA ATA GAA    1938
Gly Gly Thr Cys Lys Val Leu Gly Pro Asp Cys Cys Ile Gly Ile Glu
                1285                1290                1295

GAT CTA TCT AAA AAT ATC TCA GAA CAA ATC GAC AAA ATC AGA AAG GAT    1986
Asp Leu Ser Lys Asn Ile Ser Glu Gln Ile Asp Lys Ile Arg Lys Asp
        1300                1305                1310

GAA CAA AAG GAG GAA ACT GGC TGG GGT CTA GGT GGC AAA TGG TGG ACA    2034
Glu Gln Lys Glu Glu Thr Gly Trp Gly Leu Gly Gly Lys Trp Trp Thr
```

```
                1315                1320                1325
TCT GAC TGG GGT GTT CTC ACC AAT TTG GGC ATC CTA CTA TTA TCT        2082
Ser Asp Trp Gly Val Leu Thr Asn Leu Gly Ile Leu Leu Leu Ser
    1330                1335                1340

ATA GCT GTT CTG ATT GCT CTG TCC TGT ATC TGT CGT ATC TTC ACT AAA    2130
Ile Ala Val Leu Ile Ala Leu Ser Cys Ile Cys Arg Ile Phe Thr Lys
1345                1350                1355                1360

TAC ATT GGA TGA CATAAAGTTT ACAATGGTTA GAGCTTTAGG AAAGTTGCTG        2182
Tyr Ile Gly  *

CTGAGCCCTT TGTCTAATCT ACTGAAATCG ACTTAAAGAA TCCTCAGGGA GCTTATAACT  2242

CAATG                                                              2247
```

(2) INFORMATION FOR SEQ ID NO:6:

(i) SEQUENCE CHARACTERISTICS:
        (A) LENGTH: 681 amino acids
        (B) TYPE: amino acid
        (D) TOPOLOGY: linear (ii) MOLECULE TYPE: protein (xi) SEQUENCE DESCRIPTION: SEQ ID NO:6:

```
Met Lys Thr Ile Tyr Phe Leu Ile Ser Leu Ile Leu Ile Gln Ser Ile
 1               5                  10                  15

Lys Thr Leu Pro Val Leu Glu Ile Ala Ser Asn Ser Gln Pro Gln Asp
            20                  25                  30

Val Asp Ser Val Cys Ser Gly Thr Leu Gln Lys Thr Glu Asp Val His
        35                  40                  45

Leu Met Gly Phe Thr Leu Ser Gly Gln Lys Val Ala Asp Ser Pro Leu
    50                  55                  60

Glu Ala Ser Lys Arg Trp Ala Phe Arg Thr Gly Val Pro Pro Lys Asn
65                  70                  75                  80

Val Glu Tyr Thr Glu Gly Glu Ala Lys Thr Cys Tyr Asn Ile Ser
            85                  90                  95

Val Thr Asp Pro Ser Gly Lys Ser Leu Leu Asp Pro Pro Ser Asn
        100                 105                 110

Ile Arg Asp Tyr Pro Lys Cys Lys Thr Val His His Ile Gln Gly Gln
    115                 120                 125

Asn Pro His Ala Gln Gly Ile Ala Leu His Leu Trp Gly Ala Phe Phe
130                 135                 140

Leu Tyr Asp Arg Val Ala Ser Thr Thr Met Tyr Arg Gly Lys Val Phe
145                 150                 155                 160

Thr Glu Gly Asn Ile Ala Ala Met Ile Val Asn Lys Thr Val His Arg
            165                 170                 175

Met Ile Phe Ser Arg Gln Gly Gln Gly Tyr Arg His Met Asn Leu Thr
        180                 185                 190

Ser Thr Asn Lys Tyr Trp Thr Ser Asn Glu Thr Gln Arg Asn Asp
    195                 200                 205

Thr Gly Cys Phe Gly Ile Leu Gln Glu Tyr Asn Ser Thr Asn Asn Gln
210                 215                 220

Thr Cys Pro Pro Ser Leu Lys Pro Pro Ser Leu Pro Thr Val Thr Pro
225                 230                 235                 240

Ser Ile His Ser Thr Asn Thr Gln Ile Asn Thr Ala Lys Ser Gly Thr
            245                 250                 255

Met Asn Pro Ser Ser Asp Asp Glu Asp Leu Met Ile Ser Gly Ser Gly
        260                 265                 270
```

-continued

```
Ser Gly Glu Gln Gly Pro His Thr Thr Leu Asn Val Val Thr Glu Gln
        275                 280                 285
Lys Gln Ser Ser Thr Ile Leu Ser Thr Pro Ser Leu His Pro Ser Thr
    290                 295                 300
Ser Gln His Glu Gln Asn Ser Thr Asn Pro Ser Arg His Ala Val Thr
305                 310                 315                 320
Glu His Asn Gly Thr Asp Pro Thr Thr Gln Pro Ala Thr Leu Leu Asn
                325                 330                 335
Asn Thr Asn Thr Thr Pro Thr Tyr Asn Thr Leu Lys Tyr Asn Leu Ser
                340                 345                 350
Thr Pro Ser Pro Pro Thr Arg Asn Ile Thr Asn Asn Asp Thr Gln Arg
        355                 360                 365
Ala Thr Ser Arg Lys Arg Gln Thr Asn Ala Gln Leu Asn Thr Thr Leu
    370                 375                 380
Asp Pro Thr Glu Asn Pro Thr Thr Gly Gln Asp Thr Asn Ser Thr Thr
385                 390                 395                 400
Asn Ile Ile Met Thr Thr Ser Asp Ile Thr Ser Lys His Pro Thr Asn
                405                 410                 415
Ser Ser Pro Asp Ser Ser Pro Thr Thr Arg Pro Pro Ile Tyr Phe Arg
                420                 425                 430
Lys Lys Arg Ser Ile Phe Trp Lys Glu Gly Asp Ile Phe Pro Phe Leu
        435                 440                 445
Asp Gly Leu Ile Asn Thr Glu Ile Asp Phe Asp Pro Ile Pro Asn Thr
    450                 455                 460
Glu Thr Ile Phe Asp Glu Ser Pro Ser Phe Asn Thr Ser Thr Asn Glu
465                 470                 475                 480
Glu Gln His Thr Pro Pro Asn Ile Ser Leu Thr Phe Ser Tyr Phe Pro
                485                 490                 495
Asp Lys Asn Gly Asp Thr Ala Tyr Ser Gly Glu Asn Glu Asn Asp Cys
                500                 505                 510
Asp Ala Glu Leu Arg Ile Trp Ser Val Gln Glu Asp Asp Leu Ala Ala
            515                 520                 525
Gly Leu Ser Trp Ile Pro Phe Phe Gly Pro Gly Ile Glu Gly Leu Tyr
    530                 535                 540
Thr Ala Gly Leu Ile Lys Asn Gln Asn Asn Leu Val Cys Arg Leu Arg
545                 550                 555                 560
Arg Leu Ala Asn Gln Thr Ala Lys Ser Leu Glu Leu Leu Leu Arg Val
                565                 570                 575
Thr Thr Glu Glu Arg Thr Phe Ser Leu Ile Asn Arg His Ala Ile Asp
                580                 585                 590
Phe Leu Leu Thr Arg Trp Gly Gly Thr Cys Lys Val Leu Gly Pro Asp
        595                 600                 605
Cys Cys Ile Gly Ile Glu Asp Leu Ser Lys Asn Ile Ser Glu Gln Ile
        610                 615                 620
Asp Lys Ile Arg Lys Asp Glu Gln Lys Glu Glu Thr Gly Trp Gly Leu
625                 630                 635                 640
Gly Gly Lys Trp Trp Thr Ser Asp Trp Gly Val Leu Thr Asn Leu Gly
                645                 650                 655
Ile Leu Leu Leu Leu Ser Ile Ala Val Leu Ile Ala Leu Ser Cys Ile
                660                 665                 670
Cys Arg Ile Phe Thr Lys Tyr Ile Gly
        675                 680
```

(2) INFORMATION FOR SEQ ID NO:7:

(i) SEQUENCE CHARACTERISTICS:
        (A) LENGTH: 4326 base pairs
        (B) TYPE: nucleic acid
        (C) STRANDEDNESS: double
        (D) TOPOLOGY: circular (ii) MOLECULE TYPE: other nucleic acid
        (A) DESCRIPTION: /desc = "Expression vector
            construct"

(vii) IMMEDIATE SOURCE:
        (B) CLONE: pWRG7077

(ix) FEATURE:
        (A) NAME/KEY: promoter
        (B) LOCATION: 1250..2062

(ix) FEATURE:
        (A) NAME/KEY: intron
        (B) LOCATION: 2063..2887
        (D) OTHER INFORMATION: /function= "Human Cytomegalovirus
            Intron A"

(ix) FEATURE:
        (A) NAME/KEY: polyA_site
        (B) LOCATION: 2912..3314

(ix) FEATURE:
        (A) NAME/KEY: CDS
        (B) LOCATION: complement (299..1114)

(xi) SEQUENCE DESCRIPTION: SEQ ID NO:7:

```
GGGGGGGGGG GGCGCTGAGG TCTGCCTCGT GAAGAAGGTG TTGCTGACTC ATACCAGGCC    60

TGAATCGCCC CATCATCCAG CCAGAAAGTG AGGGAGCCAC GGTTGATGAG AGCTTTGTTG   120

TAGGTGGACC AGTTGGTGAT TTTGAACTTT GCTTTGCCA CGGAACGGTC TGCGTTGTCG    180

GGAAGATGCG TGATCTGATC CTTCAACTCA GCAAAAGTTC GATTTATTCA ACAAAGCCGC   240

CGTCCCGTCA AGTCAGCGTA ATGCTCTGCC AGTGTTACAA CCAATTAACC AATTCTGATT   300

AGAAAAACTC ATCGAGCATC AAATGAAACT GCAATTTATT CATATCAGGA TTATCAATAC   360

CATATTTTTG AAAAAGCCGT TTCTGTAATG AAGGAGAAAA CTCACCGAGG CAGTTCCATA   420

GGATGGCAAG ATCCTGGTAT CGGTCTGCGA TTCCGACTCG TCCAACATCA ATACAACCTA   480

TTAATTTCCC CTCGTCAAAA ATAAGGTTAT CAAGTGAGAA ATCACCATGA GTGACGACTG   540

AATCCGGTGA GAATGGCAAA AGCTTATGCA TTTCTTTCCA GACTTGTTCA ACAGGCCAGC   600

CATTACGCTC GTCATCAAAA TCACTCGCAT CAACCAAACC GTTATTCATT CGTGATTGCG   660

CCTGAGCGAG ACGAAATACG CGATCGCTGT TAAAAGGACA ATTACAAACA GGAATCGAAT   720

GCAACCGGCG CAGGAACACT GCCAGCGCAT CAACAATATT TTCACCTGAA TCAGGATATT   780

CTTCTAATAC CTGGAATGCT GTTTTCCCGG GGATCGCAGT GGTGAGTAAC CATGCATCAT   840

CAGGAGTACG GATAAAATGC TTGATGGTCG GAAGAGGCAT AAATTCCGTC AGCCAGTTTA   900

GTCTGACCAT CTCATCTGTA ACATCATTGG CAACGCTACC TTTGCCATGT TTCAGAAACA   960

ACTCTGGCGC ATCGGGCTTC CCATACAATC GATAGATTGT CGCACCTGAT TGCCCGACAT  1020

TATCGCGAGC CCATTTATAC CCATATAAAT CAGCATCCAT GTTGGAATTT AATCGCGGCC  1080

TCGAGCAAGA CGTTTCCCGT TGAATATGGC TCATAACACC CCTTGTATTA CTGTTTATGT  1140

AAGCAGACAG TTTTATTGTT CATGATGATA TATTTTTATC TTGTGCAATG TAACATCAGA  1200

GATTTTGAGA CACAACGTGG CTTTCCCCCC CCCCCGGCA TGCCTGCAGG TCGACAATAT  1260

TGGCTATTGG CCATTGCATA CGTTGTATCT ATATCATAAT ATGTACATTT ATATTGGCTC  1320
```

```
ATGTCCAATA TGACCGCCAT GTTGACATTG ATTATTGACT AGTTATTAAT AGTAATCAAT      1380

TACGGGGTCA TTAGTTCATA GCCCATATAT GGAGTTCCGC GTTACATAAC TTACGGTAAA      1440

TGGCCCGCCT GGCTGACCGC CCAACGACCC CCGCCCATTG ACGTCAATAA TGACGTATGT      1500

TCCCATAGTA ACGCCAATAG GGACTTTCCA TTGACGTCAA TGGGTGGAGT ATTTACGGTA      1560

AACTGCCCAC TTGGCAGTAC ATCAAGTGTA TCATATGCCA AGTCCGCCCC CTATTGACGT      1620

CAATGACGGT AAATGGCCCG CCTGGCATTA TGCCCAGTAC ATGACCTTAC GGACTTTCC       1680

TACTTGGCAG TACATCTACG TATTAGTCAT CGCTATTACC ATGGTGATGC GGTTTTGGCA      1740

GTACACCAAT GGGCGTGGAT AGCGGTTTGA CTCACGGGGA TTTCCAAGTC TCCACCCCAT      1800

TGACGTCAAT GGGAGTTTGT TTTGGCACCA AAATCAACGG GACTTTCCAA AATGTCGTAA      1860

TAACCCCGCC CCGTTGACGC AAATGGGCGG TAGGCGTGTA CGGTGGGAGG TCTATATAAG      1920

CAGAGCTCGT TTAGTGAACC GTCAGATCGC CTGGAGACGC CATCCACGCT GTTTTGACCT      1980

CCATAGAAGA CACCGGGACC GATCCAGCCT CCGCGGCCGG GAACGGTGCA TTGGAACGCG      2040

GATTCCCCGT GCCAAGAGTG ACGTAAGTAC CGCCTATAGA CTCTATAGGC ACACCCCTTT      2100

GGCTCTTATG CATGCTATAC TGTTTTTGGC TTGGGGCCTA TACACCCCCG CTTCCTTATG      2160

CTATAGGTGA TGGTATAGCT TAGCCTATAG GTGTGGGTTA TTGACCATTA TTGACCACTC      2220

CCCTATTGGT GACGATACTT TCCATTACTA ATCCATAACA TGGCTCTTTG CCACAACTAT      2280

CTCTATTGGC TATATGCCAA TACTCTGTCC TTCAGAGACT GACACGGACT CTGTATTTTT      2340

ACAGGATGGG GTCCCATTTA TTATTTACAA ATTCACATAT ACAACAACGC CGTCCCCCGT      2400

GCCCGCAGTT TTTATTAAAC ATAGCGTGGG ATCTCCACGC GAATCTCGGG TACGTGTTCC      2460

GGACATGGGC TCTTCTCCGG TAGCGGCGGA GCTTCCACAT CCGAGCCCTG GTCCCATGCC      2520

TCCAGCGGCT CATGGTCGCT CGGCAGCTCC TTGCTCCTAA CAGTGGAGGC CAGACTTAGG      2580

CACAGCACAA TGCCCACCAC CACCAGTGTG CCGCACAAGG CCGTGGCGGT AGGGTATGTG      2640

TCTGAAAATG AGCTCGGAGA TTGGGCTCGC ACCGCTGACG CAGATGGAAG ACTTAAGGCA      2700

GCGGCAGAAG AAGATGCAGG CAGCTGAGTT GTTGTATTCT GATAAGAGTC AGAGGTAACT      2760

CCCGTTGCGG TGCTGTTAAC GGTGGAGGGC AGTGTAGTCT GAGCAGTACT CGTTGCTGCC      2820

GCGCGCGCCA CCAGACATAA TAGCTGACAG ACTAACAGAC TGTTCCTTTC CATGGGTCTT      2880

TTCTGCAGTC ACCGTCCAAG CTTGCGGCCG CGGATCCTCG CAATCCCTAG GAGGATTAGG      2940

CAAGGGCTTG AGCTCACGCT CTTGTGAGGG ACAGAAATAC AATCAGGGGC AGTATATGAA      3000

TACTCCATGG AGAAACCCAG ATCTACGTAT GATCAGCCTC GACTGTGCCT TCTAGTTGCC      3060

AGCCATCTGT TGTTTGCCCC TCCCCCGTGC CTTCCTTGAC CCTGGAAGGT GCCACTCCCA      3120

CTGTCCTTTC CTAATAAAAT GAGGAAATTG CATCGCATTG TCTGAGTAGG TGTCATTCTA      3180

TTCTGGGGGG TGGGGTGGGG CAGGACAGCA AGGGGGAGGA TTGGGAAGAC AATAGCAGGC      3240

ATGCTGGGGA TGCGGTGGGC TCTATGGCTT CTGAGGCGGA AAGAACCAGC TGGGGCTCGA      3300

CAGCTCGACT CTAGAATTGC TTCCTCGCTC ACTGACTCGC TGCGCTCGGT CGTTCGGCTG      3360

CGGCGAGCGG TATCAGCTCA CTCAAAGGCG GTAATACGGT TATCCACAGA ATCAGGGGAT      3420

AACGCAGGAA AGAACATGTG AGCAAAAGGC CAGCAAAAGG CCAGGAACCG TAAAAAGGCC      3480

GCGTTGCTGG CGTTTTTCCA TAGGCTCCGC CCCCCTGACG AGCATCACAA AAATCGACGC      3540

TCAAGTCAGA GGTGGCGAAA CCCGACAGGA CTATAAAGAT ACCAGGCGTT TCCCCCTGGA      3600

AGCTCCCTCG TGCGCTCTCC TGTTCCGACC CTGCCGCTTA CCGGATACCT GTCCGCCTTT      3660
```

-continued

```
CTCCCTTCGG GAAGCGTGGC GCTTTCTCAT AGCTCACGCT GTAGGTATCT CAGTTCGGTG    3720

TAGGTCGTTC GCTCCAAGCT GGGCTGTGTG CACGAACCCC CCGTTCAGCC CGACCGCTGC    3780

GCCTTATCCG GTAACTATCG TCTTGAGTCC AACCCGGTAA GACACGACTT ATCGCCACTG    3840

GCAGCAGCCA CTGGTAACAG GATTAGCAGA GCGAGGTATG TAGGCGGTGC TACAGAGTTC    3900

TTGAAGTGGT GGCCTAACTA CGGCTACACT AGAAGAACAG TATTTGGTAT CTGCGCTCTG    3960

CTGAAGCCAG TTACCTTCGG AAAAAGAGTT GGTAGCTCTT GATCCGGCAA ACAAACCACC    4020

GCTGGTAGCG GTGGTTTTTT TGTTTGCAAG CAGCAGATTA CGCGCAGAAA AAAAGGATCT    4080

CAAGAAGATC CTTTGATCTT TTCTACGGGG TCTGACGCTC AGTGGAACGA AAACTCACGT    4140

TAAGGGATTT TGGTCATGAG ATTATCAAAA AGGATCTTCA CCTAGATCCT TTTAAATTAA    4200

AAATGAAGTT TTAAATCAAT CTAAAGTATA TATGAGTAAA CTTGGTCTGA CAGTTACCAA    4260

TGCTTAATCA GTGAGGCACC TATCTCAGCG ATCTGTCTAT TTCGTTCATC CATAGTTGCC    4320

TGACTC                                                                4326
```

(2) INFORMATION FOR SEQ ID NO:8:

(i) SEQUENCE CHARACTERISTICS:
        (A) LENGTH: 271 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ser His Ile Gln Arg Glu Thr Ser Cys Ser Arg Pro Arg Leu Asn
 1               5                  10                  15

Ser Asn Met Asp Ala Asp Leu Tyr Gly Tyr Lys Trp Ala Arg Asp Asn
             20                  25                  30

Val Gly Gln Ser Gly Ala Thr Ile Tyr Arg Leu Tyr Gly Lys Pro Asp
         35                  40                  45

Ala Pro Glu Leu Phe Leu Lys His Gly Lys Gly Ser Val Ala Asn Asp
     50                  55                  60

Val Thr Asp Glu Met Val Arg Leu Asn Trp Leu Thr Glu Phe Met Pro
 65                  70                  75                  80

Leu Pro Thr Ile Lys His Phe Ile Arg Thr Pro Asp Asp Ala Trp Leu
                 85                  90                  95

Leu Thr Thr Ala Ile Pro Gly Lys Thr Ala Phe Gln Val Leu Glu Glu
            100                 105                 110

Tyr Pro Asp Ser Gly Glu Asn Ile Val Asp Ala Leu Ala Val Phe Leu
        115                 120                 125

Arg Arg Leu His Ser Ile Pro Val Cys Asn Cys Pro Phe Asn Ser Asp
    130                 135                 140

Arg Val Phe Arg Leu Ala Gln Ala Gln Ser Arg Met Asn Asn Gly Leu
145                 150                 155                 160

Val Asp Ala Ser Asp Phe Asp Asp Glu Arg Asn Gly Trp Pro Val Glu
                165                 170                 175

Gln Val Trp Lys Glu Met His Lys Leu Leu Pro Phe Ser Pro Asp Ser
            180                 185                 190

Val Val Thr His Gly Asp Phe Ser Leu Asp Asn Leu Ile Phe Asp Glu
        195                 200                 205

Gly Lys Leu Ile Gly Cys Ile Asp Val Gly Arg Val Gly Ile Ala Asp
    210                 215                 220

Arg Tyr Gln Asp Leu Ala Ile Leu Trp Asn Cys Leu Gly Glu Phe Ser
```

```
                225                 230                 235                 240
            Pro Ser Leu Gln Lys Arg Leu Phe Gln Lys Tyr Gly Ile Asp Asn Pro
                            245                 250                 255
            Asp Met Asn Lys Leu Gln Phe His Leu Met Leu Asp Glu Phe Phe
                    260                 265                 270
```

(2) INFORMATION FOR SEQ ID NO:9:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

```
CGCGAGATCT AACATGAAGA CCACATGTTT CC                                        32
```

(2) INFORMATION FOR SEQ ID NO:10:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

```
GATCAGATCT TTATCCGATA TATTTAG                                              27
```

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

```
CGCGAGATCT ATGAAGAACA TTAATTGC                                             28
```

(2) INFORMATION FOR SEQ ID NO:12:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:12:

```
GACATGAAGA CCATATA                                                         17
```

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single (D) TOPOLOGY: linear (ii) MOLECULE TYPE: other nucleic acid
            (A) DESCRIPTION: /desc = "primer"

(xi) SEQUENCE DESCRIPTION: SEQ ID NO:13:

CTTTATGTCA TCCAATG                                                          17

(2) INFORMATION FOR SEQ ID NO:14:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:14:

GGCAATTAAG TTCTTTG                                                          17

(2) INFORMATION FOR SEQ ID NO:15:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:15:

GATCAGATCT ACAATGGGCG TTACAGG                                               27

(2) INFORMATION FOR SEQ ID NO:16:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:16:

GATCAGATCT CTAAAAGACA AATTTG                                                26

(2) INFORMATION FOR SEQ ID NO:17:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "primer"

(xi) SEQUENCE DESCRIPTION: SEQ ID NO:17:

GATCAGATCT GCGATGAAGA TTAAG                                                 25

GENETIC INDUCTION OF ANTI-VIRAL IMMUNE RESPONSE AND GENETIC VACCINE FOR FILOVIRUS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to the general field of genetic vaccines and relates, in particular, to genetic agents delivered into the skin or mucosal tissues of animals to induce an immune response, and more particularly to genetic vaccines for viral pathogens delivered into skin or mucosal tissues by particle acceleration.

In particular, the present invention relates to the field of genetic vaccines that protect human and non-human vertebrates against infection by viruses of the Filovirus genus (Family Filoviridae). The known filoviruses include the Ebola virus Reston, Ebola virus Sudan, Ebola virus Zaire and Marburg virus (strain Musoke and strain Ravn). Filoviruses are non-segmented, negative stranded enveloped ssRNA viruses having a vertebrate host range. The range of possible invertebrate hosts (such as, but not limited to, arthropods) is not known. A glycoprotein inserted in the viral envelope may mediate virus entry into host cells.

The Marburg virus glycoprotein (170 kD) is a type I transmembrane protein. The carbohydrate structures account for more than 50% of the molecular weight of the protein. The Ebola virus glycoproteins (125 kD) appear to have similar carbohydrate structures to the Marburg glycoproteins, except insofar as the Ebola glycoproteins are terminally sialated.

Marburg and Ebola viruses cause severe hemorrhagic fever in humans and in laboratory primates. Ebola-Zaire strain appears to be more deadly than either the Sudan strain or the Marburg virus. After an incubation period of four to sixteen days, sudden fever, chills, headache, anorexia and myalgia appear. Nausea, vomiting, sore throat, abdominal pain and diarrhea soon follow. Most patients develop severe hemorrhaging between about days five and seven. Death usually occurs between seven and sixteen days.

In patients, antibodies directed primarily against the surface glycoproteins of Marburg and Ebola viruses can be detected as early as ten to fourteen days after infection. However, it is not entirely clear that such antibodies can prevent the overt manifestations of the disease.

The vaccination of individuals to render the vaccinated individuals resistant to the development of infectious disease is one of the oldest forms of preventive care in medicine. Previously, vaccines for viral and bacterial pathogens for pediatric, adult, and veterinary usage were derived directly from the infectious organisms and could be categorized as falling into one of three broad categories: live attenuated, killed, and subunit vaccines. Although the three categories of vaccines differ significantly in their development and mode of actions, the administration of any of these three categories of these vaccines is intended to result in production of specific immunological responses to the pathogen, following one or more inoculations of the vaccine. The resulting immunological responses may or may not completely protect the individual against subsequent infection, but will usually prevent the manifestation of disease symptoms and significantly limit the extent of any subsequent infection.

The techniques of modern molecular biology have enabled a variety of new vaccine strategies to be developed which are in various stages of pre-clinical and clinical development. The intent of these efforts is not only to produce new vaccines for old diseases, but also to yield new vaccines for infectious diseases in which classical vaccine development strategies have so far proven unsuccessful. Notably, the recent identification and spread of immunodeficiency viruses is an example of a pathogen for which classical vaccine development strategies have not yielded effective control to date.

The first broad category of classical vaccine is live attenuated vaccines. A live attenuated vaccine represents a specific strain of the pathogenic virus, or bacterium, which has been altered so as to lose its pathogenicity, but not its ability to infect and replicate in humans. Live attenuated vaccines are regarded as the most effective form of vaccine because they establish a true infection within the individual. The replicating pathogen and its infection of human cells stimulates both humoral and cellular compartments of the immune system as well as long-lasting immunological memory. Thus, live attenuated vaccines for viral and intracellular bacterial infections stimulate the production of neutralizing antibodies, as well as cytotoxic T-lymphocytes (CTLs), usually after only a single inoculation.

The ability of live attenuated vaccines to stimulate the production of CTLs is believed to be an important reason for the comparative effectiveness of live attenuated vaccines. CTLs are recognized as the main component of the immune system responsible for the actual clearing of viral and intracellular bacterial infections. CTLs are triggered by the production of foreign proteins in individual infected cells of the hosts, the infected cells processing the antigen and presenting the specific antigenic determinants on the cell surface for immunological recognition.

The induction of CTL immunity by attenuated vaccines is due to the establishment of an actual, though limited, infection in the host cells including the production of foreign antigens in the individual infected cells. The vaccination process resulting from a live attenuated vaccine also results in the induction of immunological memory, which manifests itself in the prompt expansion of specific CTL clones and antibody-producing plasma cells in the event of future exposure to a pathogenic form of the infectious agent, resulting in the rapid clearing of this infection and practical protection from disease.

An important disadvantage of live attenuated vaccines is that they have an inherent tendency to revert to a new virulent phenotype through random genetic mutation. Although statistically such a reversion is a rare event for attenuated viral vaccines in common use today, such vaccines are administered on such a large scale that occasional reversions are inevitable, and documented cases of vaccine-induced illnesses exist. In addition, complications are sometimes observed when attenuated vaccines lead to the establishment of disseminated infections due to a lowered state of immune system competence in the vaccine recipient. Further limitations on the development of attenuated vaccines are that appropriate attenuated strains can be difficult to identify for some pathogens and that the frequency of mutagenic drift for some pathogens can be so great that the risk associated with reversion are simply unacceptable. A virus for which this latter point is particularly well exemplified is the human immunodeficiency virus (HIV) in which the lack of an appropriate animal model, as well as an incomplete understanding of its pathogenic mechanism, makes the identification and testing of attenuated mutant virus strains effectively impossible. Even if such mutants could be identified, the rapid rate of genetic drift and the tendency of retroviruses, such as HIV, to recombine would likely lead to an unacceptable level of instability in any attenuated phenotype of the virus. Due to these complications, the production of a live attenuated vaccine for certain viruses may be unacceptable, even though this approach efficiently produces the desired cytotoxic cellular immunity and immunological memory.

The second category of vaccines consists of killed and subunit vaccines. These vaccines consist of inactivated whole bacteria or viruses, or their purified components. These vaccines are derived from pathogenic viruses or bacteria which have been inactivated by physical or chemical processing, and either the whole microbial pathogen, or a purified component of the pathogen, is formulated as the vaccine. Vaccines of this category can be made relatively safe, through the inactivation procedure, but there is a trade-off between the extent of inactivation and the extent of the immune system reaction induced in the vaccinated patient. Too much inactivation can result in extensive changes in the conformation of immunological determinants such that subsequent immune responses to the product are not protective. This is best exemplified by clinical evaluation of inactivated measles and respiratory syncytial virus vaccines in the past, which resulted in strong antibody responses which not only failed to neutralize infectious virions, but exacerbated disease upon exposure to infectious virus. On the other extreme, if inactivating procedures are kept at a minimum to preserve immunogenicity, there is significant risk of incorporating infectious material in the vaccine formulation.

The main advantage of killed or subunit vaccines is that they can induce a significant titer of neutralizing antibodies in the vaccinated individual. Killed vaccines are generally more immunogenic than subunit vaccines, in that they elicit responses to multiple antigenic sites on the pathogen. Killed virus or subunit vaccines routinely require multiple inoculations to achieve the appropriate priming and booster responses, but the resultant immunity can be long lasting. These vaccines are particularly effective at preventing disease caused by toxin-producing bacteria, where the mode of protection is a significant titer of toxin neutralizing antibody. The antibody response can last for a significant period or can rapidly rebound upon subsequent infection, due to an anamnestic or secondary response. On the other hand, these vaccines generally fail to produce a cytotoxic cellular immune response, making them less than ideal for preventing viral disease. Since cytotoxic lymphocytes are the primary vehicle for the elimination of viral infections, any vaccine strategy which cannot stimulate cytotoxic cellular immunity is usually the less preferred methodology for a virus disease, thereby resulting in attenuated virus being the usual methodology of choice.

The development of recombinant DNA technology has now made possible the heterologous production of any protein, of a microbial or viral pathogen, or part thereof, to be used as a vaccine. The vaccine constituents thus do not need to be derived from the actual pathogenic organism itself. In theory, for example, viral surface glycoproteins can be produced in eukaryotic expression systems in their native conformation for proper immunogenicity. However, in practice, recombinant viral protein constituents do not universally elicit protecting antibody responses. Further, as with killed vaccines, cellular cytotoxic immune responses are generally not seen after inoculation with a recombinant subunit protein. Thus, while this vaccine strategy offers an effective way of producing large quantities of a safe and potentially immunogenic viral or bacterial protein, such vaccines are capable of yielding only serum antibody responses and thus may not be the best choice for providing protection against viral disease.

The availability of recombinant DNA technology and the developments in immunology have led to the immunological fine mapping of the antigenic determinants of various microbial antigens. It is now theoretically possible, therefore, to develop chemically synthetic vaccines based on short peptides in which each peptide represents a distinct epitope or determinant. Progress has been made in identifying helper T-cell determinants, which are instrumental in driving B-cell or antibody immune responses. The covalent linkage of a helper T-cell peptide to a peptide representing a B-cell epitope, or antibody binding site, can dramatically increase the immunogenicity of the B-cell epitope. Unfortunately, many natural antibody binding sites on viruses are conformation-dependent, or are composed of more than one peptide chain, such that the structure of the epitope on the intact virus becomes difficult to mimic with a synthetic peptide. Thus peptide vaccines do not appear to be the best vehicle for the stimulation of neutralizing antibodies for viral pathogens. On the other hand, there is some preliminary evidence that peptides representing the determinants recognized by cytotoxic T-lymphocytes can induce CTLs, if they are targeted to the membranes of cells bearing Class I Major Histocompatibility Complex (MHC) antigens, via coupling to a lipophilic moiety. These experimental peptide vaccines appear safe and inexpensive, but have some difficulty in mimicking complex three dimensional protein structures, although there is some evidence that they can be coaxed into eliciting cytotoxic immunity in experimental animals.

Another new recombinant technique which has been proposed for vaccines is to create live recombinant vaccines representing non-pathogenic viruses, such as a vaccinia virus or adenovirus, in which a segment of the viral genome has been replaced with a gene encoding a viral antigen from a heterologous, pathogenic virus. Research has indicated that infection of experimental animals with such a recombinant virus leads to the production of a variety of viral proteins, including the heterologous protein. The end result is usually a cytotoxic cellular immune response to the heterologous protein caused by its production after inoculation. Often a detectable antibody response is seen as well. Live recombinant viruses are, therefore, similar to attenuated viruses in their mode of action and result in immune responses, but do not exhibit the tendency to revert to a more virulent phenotype. On the other hand, the strategy is not without disadvantage in that vaccinia virus and adenovirus, though non-pathogenic, can still induce pathogenic infections at a low frequency. Thus it would not be indicated for use with immune-compromised individuals, due to the possibility of a catastrophic disseminated infection. In addition, the ability of these vaccines to induce immunity to a heterologous protein may be compromised by pre-existing immunity to the carrier virus, thus preventing a successful infection with the recombinant virus, and thereby preventing production of the heterologous protein.

In summary, all of the vaccine strategies described above possess unique advantages and disadvantages which limit their usefulness against various infectious agents. Several strategies employ non-replicating antigens. While these strategies can be used for the induction of serum antibodies which may be neutralizing, such vaccines require multiple inoculations and do not produce cytotoxic immunity. For viral diseases, attenuated viruses are regarded as the most effective, due to their ability to produce potent cytotoxic immunity and lasting immunological memory. However, safe attenuated vaccines cannot be developed for all viral pathogens.

It is therefore desirable that vaccines be developed which are capable of producing cytotoxic immunity, immunological memory, and humoral (circulating) antibodies, without having any unacceptable risk of pathogenicity, or mutation, or recombination of the virus in the vaccinated individual.

To date, no pharmaceutical or immunological methods exist for preventing filovirus infections or for intervening after infection. Vaccination with viral antigens or inactivated whole virus vaccines have been ineffective in protecting against challenge with live virus. No antiviral drug has been effective, even in vitro. Thus, no specific treatments exist for the diseases caused by filoviruses.

Published PCT patent application Nos. PCT/US93/02394 and PCT/US93/02338, both incorporated herein by reference, relate to genetic immunizations for viruses using viral DNA.

BRIEF SUMMARY OF THE INVENTION

The present invention is summarized in that an animal is vaccinated against a filovirus by a genetic vaccination method that includes the steps of preparing copies of a foreign genetic construction including a promoter operative in cells of the animal and a protein-coding region coding for a glycoprotein produced by the filovirus, and delivering the foreign genetic construction into the epidermis or mucosal tissue of the animal using a particle acceleration device.

The present invention is also summarized in that a genetic vaccine for a filovirus is created by joining a DNA sequence encoding at least a portion of the filovirus glycoprotein to a promoter effective to promote transcription of the DNA sequence in vertebrate cells, to make a genetic vaccine and then delivering the genetic vaccine into cells of an individual by a particle-mediated gene transfer process.

It is an object of the present invention to enable an effective deterrent to filovirus infection.

It is an object of the present invention to enable the induction of a protective immune response in a vaccinated individual to a filovirus through the use of a genetic vaccine.

It is a feature of the present invention in that it is adapted to either epidermal or mucosal delivery of the genetic vaccine or delivery into peripheral blood cells, and thus may be used to induce humoral, cell-mediated, and secretory immune responses in the treated individual.

It is an advantage of the genetic vaccination method of the present invention in that it is inherently safe, is not painful to administer, and should not result in adverse consequences to vaccinated individuals. The invention does not require growth or use of filoviruses, which may be spread by aerosol transmission and are typically fatal.

Other objects, advantages and features of the present invention will become apparent from the following specification.

The present invention is summarized in that the construct is coated onto the surface of small carrier particles and delivered into an animal epidermal tissue in a method for immunizing an animal against filovirus infection.

BRIEF DESCRIPTION OF THE SEVERAL VIEWS OF THE DRAWINGS

FIG. 2 illustrates the ELISA titers of anti-Marburg Musoke glycoprotein antibodies present after each immunization in control and test guinea pigs that survived or did not survive subsequent challenge with Marburg Musoke virus.

FIG. 3 illustrates the ELISA titers of anti-Marburg Musoke or anti-Marburg Ravn glycoprotein antibodies present in guinea pigs immunized with the glycoprotein-encoding gene of either Marburg Musoke, Marburg Ravn, or both. The guinea pigs were challenged with Marburg Musoke virus.

FIG. 4 illustrates the ELISA titers of anti-Marburg Musoke or anti-Marburg Ravn glycoprotein antibodies present in guinea pigs immunized with the glycoprotein-encoding gene of either Marburg Musoke, Marburg Ravn, or both. The guinea pigs were challenged with Marburg Ravn virus.

FIG. 5 shows the pre- and post-challenge ELISA titers of guinea pigs that survived challenge with a Marburg virus.

FIG. 6 shows the survival of mice immunized twice or three times with a genetic vaccine encoding the Ebola glycoprotein. Survival of between about 70 and 75% was observed in immunized animals. Control animals were not protected.

FIG. 7 depicts the ELISA titers of mice immunized twice with the Ebola glycoprotein construct.

FIG. 8 depicts the ELISA titers of mice immunized three times with the Ebola glycoprotein construct.

DETAILED DESCRIPTION OF THE INVENTION

Figure 1:
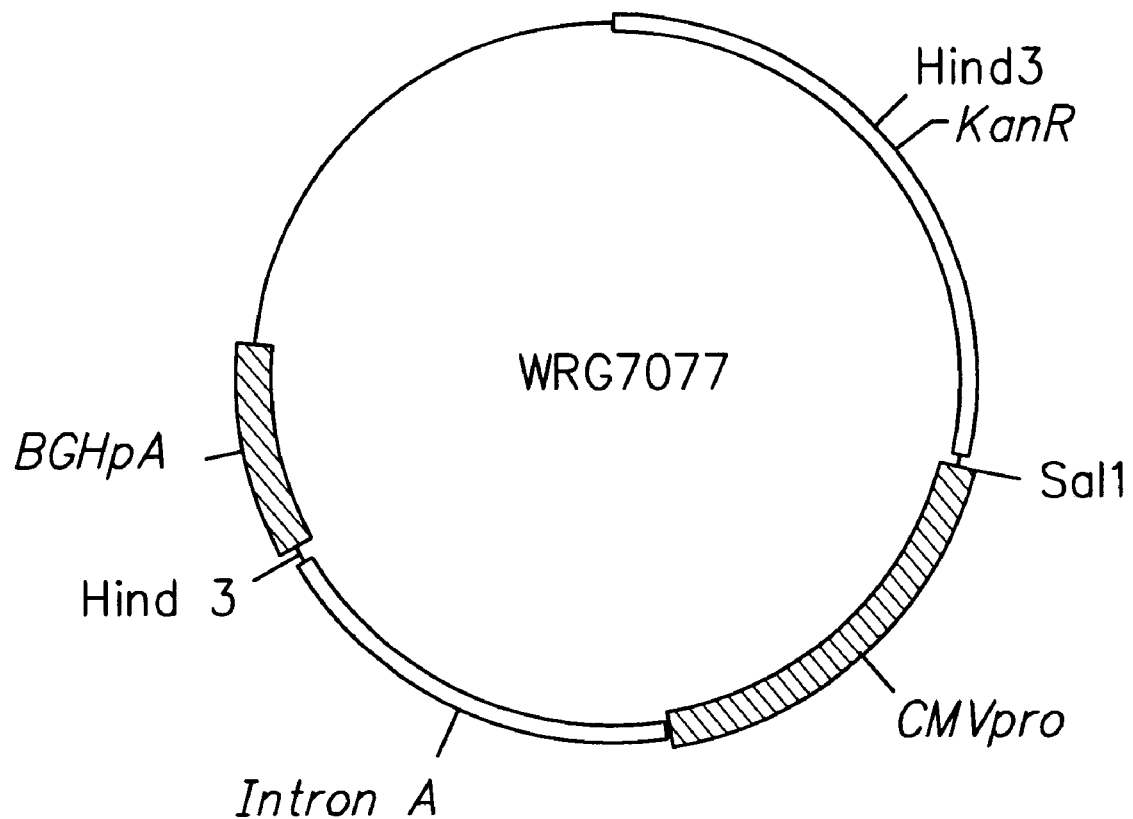
FIG. 1 is a plasmid map, showing genes and restriction sites, of the plasmid pWRG7077.

The method described here enables the creation of an immune response to a filovirus glycoprotein antigen by delivery of a viral gene encoding the antigenic protein into the epidermis or mucosal tissue of a human or non-human patient. The epidermis has now been identified as a highly advantageous target site for such a technique. The present invention is also intended to create genetic vaccines for filoviral pathogens by transfecting epidermal cells of the animal to be immunized with a gene sequence capable of causing expression in the animal cells of a portion of an antigenically-intact glycoprotein, the gene sequence not including elements of the filovirus genome necessary for replication or pathogenesis.

DNA immunization, also referred to as genetic immunization, offers a new approach for realizing the advantages of an attenuated, live, or recombinant virus vaccine by mimicking the de novo antigen production and MHC class I-restricted antigen presentation obtainable with live vaccines, without the risks of pathogenic infection in either healthy or immune-compromised individuals which are otherwise associated with the use of infectious agents. DNA immunization involves administering an antigen-encoding expression vector(s) in vivo to induce the production of a correctly folded antigen(s) within the target cells. The introduction of the genetic vaccine will cause to be expressed within those cells the structural protein determinants associated with the pathogen protein or proteins. The processed structural proteins will be displayed on the cellular surface of the transfected cells in conjunction with the Major Histocompatibility Complex (MHC) antigens of the normal cell. The display of these antigenic determinants in association with the MHC antigens is intended to elicit the proliferation of cytotoxic T-lymphocyte clones specific to the determinants. Furthermore, the structural proteins released by the expressing transfected cells can also be picked up by antigen-presenting cells to trigger systemic humoral antibody responses.

For several reasons, the genetic vaccine approach of the present invention is particularly advantageously used for vaccination against filoviruses. Filoviruses do not lend themselves to attenuated vaccine approaches due to the inherent possibility of a low percentage of the virus escaping the attenuation procedure. Filoviruses, even in very low numbers, can rapidly induce lethality. No risk of exposure to unattenuated Marburg or Ebola virus is acceptable. While viral protein subunit vaccines for these viruses are under development, such subunit vaccines may not protect animals from the severe effects of infection, including death. Subunit vaccines cannot produce a cytotoxic response, which may be necessary to prevent the establishment of filovirus infection or disease. In contrast, the use of a genetic vaccine transfection strategy as described here would trigger a cytotoxic response. Also, this genetic vaccine approach allows for delivery to mucosal tissues which may aid in conferring resistance to viral introduction. Filoviruses may enter the body through mucosal tissues.

In order to achieve the immune response sought in the vaccination process of the present invention, a genetic vaccine construction must be created which is capable of causing transfected cells of the vaccinated individual to express one or more major viral antigenic determinants. This can be done by identifying the regions of the viral genomes that encode the viral glycoproteins, obtaining coding sequences for such proteins, and joining such coding sequences to promoters capable of expressing the sequences in mammalian cells. Alternatively, the viral genome itself, or parts of the genome, can be used.

The viral genetic material used must be altered to prevent the pathogenic process from beginning. The precise method of altering the virus can vary among filoviruses and among isolates. The genetic material that encodes the single envelope glycoprotein can be used effectively. Individual expression vectors capable of expressing the genetic material can be produced using standard recombinant techniques.

A first such coding vector can include the Ebola virus glycoprotein gene or an antigenic portion thereof. The coding region encoding the Ebola virus glycoprotein begins at nucleotide 6040 and extends through nucleotide 8070 of the sequence accorded Genbank Accession Number L11365 (Ebola virus Zaire). Suitable fragments of genetic material that have been used in the present invention begin either at nucleotide 5899 or nucleotide 6035 and terminate at nucleotide 8070 of L11365. The gene is shown in SEQ ID: No 1. In SEQ ID No: 1, these preferred fragments begin either at nucleotide 4 or 142 and terminate at nucleotide 2172. The longer of these fragments contains 5' untranslated DNA. Other fragments may also be suitable.

A second such expression vector can include the gene that encodes the glycoprotein of Marburg Musoke virus or a portion thereof. The coding sequence encoding the Marburg Musoke virus glycoprotein begins at nucleotide 5940 and terminates at nucleotide 7985 of the sequence presented in Genbank Accession Number Z12132. Suitable fragments of genetic material encoding the glycoprotein commence either at nucleotide 5821 or 5938, and terminate at nucleotide 7985 of the Z12132 sequence. The Marburg Musoke glycoprotein gene is shown in SEQ ID No: 3. In SEQ ID No: 3, these preferred fragments begin either at nucleotide 1 or 119 and terminate at the end of the sequence. Other fragments may also be suitable.

A third such expression vector can include the gene that encodes the Marburg Ravn glycoprotein. The nucleotide sequence of the Ravn glycoprotein is shown in SEQ ID No: 5. The coding region for the Ravn glycoprotein extends from nucleotide 94 to nucleotide 2139 of SEQ ID No: 5. A longer fragment extending from nucleotide 1 to 2139 is also suitable, as are other fragments.

The exemplified fragments can be obtained using PCR amplification of a portion of a genomic DNA clone using the following PCR primers. To obtain the Marburg Musoke coding region on a fragment, the following primers are used: 5'-CGCGAGATCTAACATGAAGACCACATGTTTCC-3' (SEQ ID NO: 9) and 5'-GATCAGATCTTTATCCGATATATTTAG-3' (SEQ ID NO: 10). To obtain a fragment of Marburg Musoke that includes both the coding region and a 5' untranslated region, the following primer can be used in conjunction with the primer of SEQ ID NO: 10: 5'-CGCGAGATCTATGAAGAACATTAATTGC-3' (SEQ ID NO: 11). Primers can include additional non-complimentary sequences that are fixed during amplification to facilitate subsequent cloning steps.

To obtain Marburg Ravn virus glycoprotein coding region by PCR amplification, the following primers can be used: 5'-GACATGAAGACCATATA-3' (SEQ ID NO: 12) and 5'-CTTTATGTCATCCAATG-3' (SEQ ID NO: 13). To obtain the Ravn glycoprotein coding region with 5' untranslated sequence, the following primer can be used in conjunction with SEQ ID NO: 13: 5'-GGCAATTAAGTTCTTTG-3' (SEQ ID NO: 14).

To obtain Ebola virus Zaire glycoprotein coding region by PCR amplification, the following primers can be used: 5'-GATCAGATCTACAATGGGCGTTACAGG-3' (SEQ ID NO: 15) and 5'-GATCAGATCTCTAAAAGACAAATTTG-3' (SEQ ID NO: 16). To obtain the Ravn glycoprotein coding region with 5' untranslated sequence, the following primer can be used in conjunction with SEQ ID NO: 16: 5'-GATCAGATCTGCGATGAAGATTAAG-3' (SEQ ID NO: 17).

It is understood in the art that certain changes to the nucleotide sequence employed in a genetic construct have little or no bearing on the proteins encoded by the construct. Such changes result either from silent point mutations or point mutations that encode different amino acids that do not appreciably alter the behavior of the encoded protein. It is also understood that portions of the coding region can be eliminated without affecting the ability of the construct to achieve the desired effect, namely induction of a protective immune response against a filovirus challenge. It is further understood in the art that certain advantageous steps can be taken to increase the antigenicity of an encoded protein by modifying its amino acid composition. Such changes in amino acid composition can be introduced by modifying the genetic sequence encoding the protein. It is contemplated that all such modifications and variations of the filovirus glycoprotein genes are equivalents within the scope of the present invention.

To properly express the viral genetic sequence in transfected cells, the sequence is provided on a suitable expression vector. A promoter sequence operable in the target cells is needed on the vector. Several such promoters are known for mammalian systems which may be joined 5', or upstream, of the coding sequence for the protein to be expressed. A suitable promoter is the human cytomegalovirus immediate early promoter. A downstream transcriptional terminator, or polyadenylation sequence, such as the polyA addition sequence of the bovine growth hormone gene, may also be added 3' to the protein coding sequence.

A suitable construct for use in the method of the present invention is pWRG7077 (4326 bp), FIG. 1, the complete nucleotide sequence of which is shown as SEQ ID No: 7. pWRG7077 includes a human cytomegalovirus (hCMV) immediate early promoter and a bovine growth hormone polyA addition site. Between the promoter and the polyA addition site is Intron A, a sequence that naturally occurs in conjunction with the HCMV IE promoter that has been demonstrated to increase transcription when present on an expression plasmid. Downstream from Intron A, and between Intron A and the polyA addition sequence, are unique cloning sites into which the glycoprotein-encoding fragment can be cloned. The unique cloning sites include BamHI at 2912 and NotI at 2904. Also provided on pWRG7077 is a gene that confers host-cell resistance to kanamycin. Any of the fragments that encode a filovirus glycoprotein can be cloned into one of the cloning sites in pWRG7077, using methods known to the art.

It is also specifically envisioned that a single genetic vaccination can include several DNAs encoding different antigenic determinants, from the same or different viruses. For example, it may be desirable to include several DNAs to include genes for several different virus types or isolates that do not exhibit antigenic crossreactivity. Genetic constructs encoding the glycoproteins of both viruses can be combined in a single vaccine preparation. The vaccine preparation can also include genes from entirely different viruses in a single particle mediated treatment. The different genes can be combined by coating the different genes on the same carrier particles, or by mixing coated carrier particles carrying different genes for common delivery.

Separate vaccines against each type of filovirus (e.g., Marburg and Ebola) are preferred, although it may be possible to achieve protective crossreactivity across types by utilizing an antigenic portion of a filovirus glycoprotein gene common to more than one type. Some cross-protection can also be observed using a genetic vaccine derived from a single virus. For example, Marburg Musoke and Marburg Ravn viruses, show no antigenic crossreactivity, yet some crossprotection can be observed after vaccination using the present method. Cross-protection has not been observed between Ebola and Marburg.

In the present invention, the genetic construct containing the filovirus sequence is transferred into the susceptible individual by means of an accelerated particle gene transfer device. The technique of accelerated-particle gene delivery is based on the coating of genetic constructions to be delivered into cells onto extremely small carrier particles, which are designed to be small in relation to the cells sought to be transformed by the process. The coated carrier particles are then physically accelerated toward the cells to be transformed such that the carrier particles lodge in the interior of the target cells. This technique can be used either with cells in vitro or in vivo. At some frequency, the DNA which has been previously coated onto the carrier particles is expressed in the target cells. This gene expression technique has been demonstrated to work in procaryotes and eukaryotes, from bacteria and yeasts to higher plants and animals. Thus, the accelerated particle method provides a convenient methodology for delivering genes into the cells of a wide variety of tissue types, and offers the capability of delivering those genes to cells in situ and in vivo without any adverse impact or effect on the treated individual. Therefore, the accelerated particle method is also preferred in that it allows a genetic vaccine construction capable of eliciting an immune response to be directed both to a particular tissue, and to a particular cell layer in a tissue, by varying the delivery site and the force with which the particles are accelerated, respectively. This technique is thus particularly suited for delivery of genes for antigenic proteins into the epidermis.

It is also specifically envisioned that aqueous droplets containing naked DNA, including the viral genetic vaccine therein, can be delivered by suitable acceleration techniques into the tissues of the individual sought to be vaccinated. At some frequency, such "naked" DNA will be taken up in the treated tissues.

The general approach of accelerated particle gene transfection technology is described in U.S. Pat. No. 4,945,050 to Sanford. An instrument based on an improved variant of that approach is available commercially from BioRad Laboratories. An alternative approach to an accelerated particle transfection apparatus is disclosed in U.S. Pat. No. 5,015,580 which, while directed to the transfection of soybean plants, describes an apparatus which is equally adaptable for use with mammalian cells and intact whole mammals. U.S. Pat. No. 5,149,655 describes a convenient hand-held version of an accelerated particle gene delivery device. Other such devices can be based on other propulsive sources using, for example, compressed gas as a motive force. A preferred apparatus and method for delivering genetic material in the present invention is described in published PCT patent application PCT/US95/00780 and in U.S. Pat. No. 5,584,807 which will issue on Dec. 17, 1996. Both are incorporated herein by reference. Briefly, the DNA to be delivered is coated onto small (typically 1–3µ) carrier particles. The coated particles are deposited onto the interior surface of plastic tubing which is cut to a suitable length to form sample cartridges. A sample cartridge is placed in the path of a compressed gas (e.g., helium at a pressure sufficient to dislodge the particles from the cartridge (e.g., 350–400 psi). The particles are entrained in the gas stream and are delivered with sufficient force toward the target tissue to enter the cells of the tissue. Further details are available in the published patent application. A commercial embodiment of the apparatus described therein is available from Bio-Rad Laboratories, Hercules, Calif., under the name Helios.

A genetic vaccine can be delivered in a non-invasive manner to a variety of susceptible tissue types in order to achieve the desired antigenic response in the individual. Most advantageously, the genetic vaccine can be introduced into the epidermis. Such delivery, it has been found, will produce a systemic humoral immune response, a memory response, and a cytotoxic immune response. When delivering a genetic vaccine to skin cells, it was once thought desirable to remove or perforate the stratum corneum. This was accomplished by treatment with a depilatory, such as Nair. Current thought is that this step is not really necessary.

To obtain additional effectiveness from this technique, it may also be desirable that the genes be delivered to a mucosal tissue surface, in order to ensure that mucosal, humoral and cellular immune responses are produced in the vaccinated individual. It is envisioned that there are a variety of suitable delivery sites available including any number of sites on the epidermis, peripheral blood cells, i.e. lymphocytes, which could be treated in vitro and placed back into the individual, and a variety of oral, upper respiratory, and genital mucosal surfaces.

Gene gun-based DNA immunization achieves direct, intracellular delivery of expression vectors, elicits higher levels of protective immunity, and requires approximately three orders of magnitude less DNA than methods employing standard inoculation.

Moreover, gene gun delivery allows for precise control over the level and form of antigen production in a given epidermal site because intracellular DNA delivery can be controlled by systematically varying the number of particles delivered and the number of plasmid copies per particle. This precise control over the level and form of antigen production may allow for control over the nature of the resultant immune response.

The term transfected is used herein to refer to cells which have incorporated the delivered foreign genetic vaccine construction, whichever delivery technique is used. The term transfection is used in preference to the term transformation, to avoid the ambiguity inherent in the latter term, which is also used to refer to cellular changes in the process of oncogenesis.

It is herein disclosed that when inducing cellular, humoral, and protective immune responses after genetic vaccination the preferred target cells are epidermal cells, rather than cells of deeper skin layers such as the dermis. Epidermal cells are preferred recipients of genetic vaccines because they are the most accessible cells of the body and may, therefore, be immunized non-invasively. Secondly, in addition to eliciting a humoral immune response, genetically immunized epidermal cells also elicit a cytotoxic immune response that is stronger than that generated in subepidermal cells. Thus, quite unexpectedly, the epidermis is the preferred target site for genes for antigenic proteins. Contrary to what some might think, a higher immune response is elicited by epidermal delivery than to any other tissue stratum yet tested. Delivery to epidermis also has the advantages of being less invasive and delivering to cells which are ultimately sloughed by the body.

Figure 2:
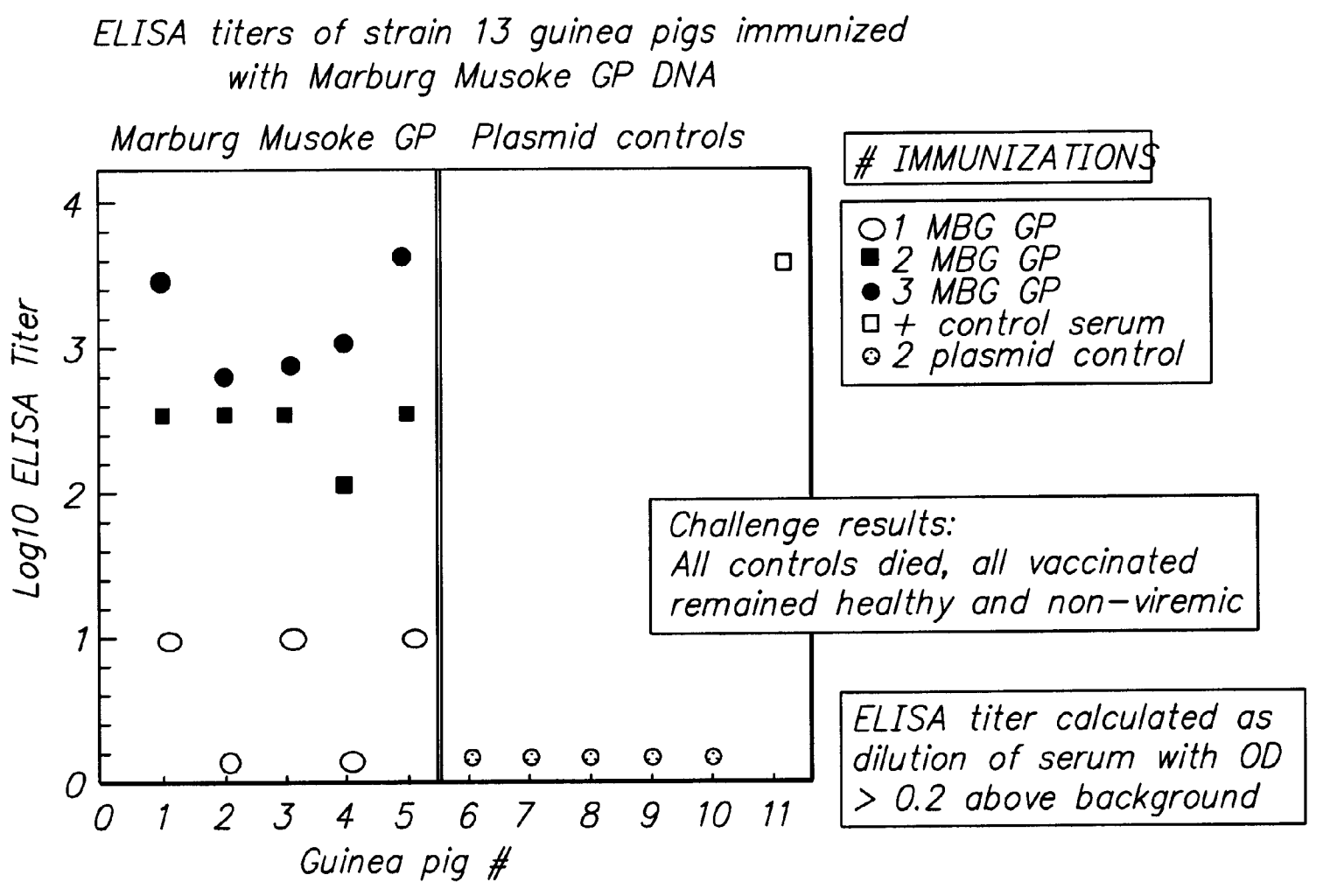

Although it can be desirable to induce an immune response by delivering genetic material to a target animal, merely demonstrating an immune response is not necessarily sufficient to confer protective advantage on the animal. What is important is to achieve a protective immune response that manifests itself in a clinical difference. That is, a method is effective only if it reduces the severity of the disease symptoms. It is preferred that the method reduce the hemorrhaging effects of virus infection when compared to unimmunized patients. It is also preferred that the immunization method be at least 20% effective in preventing death in an immunized population after challenge with a filovirus. More preferably, the vaccination method is 50% or more effective, and most preferably 70–100% effective, in preventing death in an immunized population. The vaccination method is shown herein to be 100% effective in the guinea pig model for infection with Marburg virus. In contrast, unimmunized animals are uniformly killed by challenge with Marburg virus. It is also demonstrated herein that no strong correlation exists between the level of virus glycoprotein-specific antibody and survival (FIG. 2). Thus, one would not have predicted the success of this method had one only observed the induction of an immune response.

Inasmuch as DNA immunization has proven successful in eliciting humoral, cytotoxic, and protective immune responses following gene gun-based DNA delivery to the skin and following direct injection by a variety of routes, it is also probable that DNA delivery to mucosal surfaces will result in immune responses as well. Since mucosal tissues are known entry points for certain viruses, particularly immunodeficiency viruses, mucosal tissues are a second preferred target for the genetic vaccines described herein.

Accelerated particle-based DNA delivery techniques are particularly well suited for developing protocols for genetic immunizations. The ability to penetrate deep into monkey epidermal and dermal tissues using 1–3 micron gold powder has already been established. It may be necessary to examine several depths of penetration as it is unlikely that the optimal penetration depth in mucosal tissue will mirror that seen in skin. Successful immunization may be monitored by comparing survival of immunized animals to survival of control animals, after challenge with one or more filoviruses.

The adequacy of the pathogen vaccine expression vectors to be transfected into cells can also be assessed by monitoring viral antigen production and antibody production in vivo after delivery of the genetic vaccine by particle acceleration or other method. Antigen monitoring techniques include RIA, ELISA, Western blotting, or reverse transcriptase assay. One may monitor antibody production directed against the antigen produced by the genetic vaccine using any of a number of antibody detection methods known to the art, such as ELISA, Western Blot, or neutralization assay.

The adequacy of the pathogen vaccine expression vectors to be transfected into cells can be assessed by assaying for viral antigen production in mammalian cells in vitro. Susceptible mammalian cells of a cell type which can be maintained in culture, such as monkey COS cells, can be transfected in vitro by any of a number of cell transfection techniques, including calcium phosphate-mediated transfection, as well as accelerated particle transfection. Once the genetic vaccine expression vector is introduced into the susceptible cells, the expression of the viral antigens can then be monitored in medium supernatants of the culture of such cells by a variety of techniques including ELISA and Western blotting.

After confirmation that a given expression vector is effective in inducing the appropriate viral protein production in cultured cells in vitro, it can then be demonstrated that such a vector serves to induce similar protein production in a suitable small animal model. In the case of Marburg virus, Strain 13 or Hartley guinea pigs (commercially available from Crest Caviary and Charles River Laboratory, respectively) are suitable model animals. In the case of Ebola virus, suitable animal models are Strain 13 guinea pigs or Balb/c mice susceptible to intraperitoneal infection with an Ebola virus that kills mice. Such a virus can be readily selected by serial passage of Ebola Zaire in Balb/c mice. The measurement of antigen expression and of antibody and cytotoxic cellular immune responses in the animal model system in response to such a genetic vaccine would be an important demonstration of the concept, and justifies more rigorous testing in an appropriate animal challenge model, such as susceptible monkeys before testing and use in humans.

It is also possible to detect the cell-mediated cytotoxic response, using standard methodologies known to those of ordinary skill in immunological biology. Specifically, the presence of cytotoxic T-cells in the spleen or peripheral blood can be indicated by the presence of lytic activity, which recognizes histocompatible target cells which are themselves expressing the viral antigens from the virus. Cell-mediated immunity directed against the antigen may be observed by co-cultivating responder splenocytes from vaccinated animals with stimulator splenocytes from naive syngeneic animals. Stimulator splenocytes are pretreated with mitomycin C and are coated with a antigenic epitope like that putatively produced in the vaccinated animal. Following several days of stimulation, the lytic activity of the responder splenocytes is determined by adding them at various ratios to a culture containing syngeneic target cells, coated with the antigenic epitope, and radiolabeled with $^{51}Cr$. One may determine the extent of cytotoxic lysis in the culture by measuring the extent of release of label from the target cells into the supernatant.

After then confirming that a given expression vector is effective in inducing the appropriate viral protein production and immune response in a model laboratory animal, it then becomes necessary to determine the dosage and timing suitable to produce meaningful immune responses in an animal model for viral disease. Animals would receive several doses of the expression constructs by gene delivery techniques at a variety of tissue sites. The treated tissue sites would include, but would not be limited to, the epidermis, dermis (through the epidermis), the oral cavity and upper respiratory mucosa, gut associated lymphoid tissue, and peripheral blood cells. As stated above, epidermis is the preferred target. Various challenge techniques would be utilized, and the number and timing of doses of a genetic vaccine would be systematically varied in order to optimize any resulting immunogenic response, and to determine which dosage routines resulted in maximum response. Antibody responses in the treated individuals can be detected by any of the known techniques for recognizing antibodies to specific viral antigens, again using standard Western blot and ELISA techniques.

While the best tissue sites for the delivery of a genetic vaccine for viral disease and the number and timing of doses must be empirically determined in an animal model and later confirmed in clinical studies, it is difficult at this point to predict the precise manner in which such a vaccine would be used in an actual human health care setting.

It is also important to consider that no single vaccine strategy may in itself be capable of inducing the variety of immunological responses necessary to either achieve prophylaxis in healthy individuals or forestall progression of disease in infected patients. Rather, a combination of approaches may demonstrate a true synergy in achieving these goals. Thus, it is conceivable that a combined vaccine approach incorporating a genetic vaccine, which mimics a true infection, and other approaches in combination may be an attractive way to efficiently achieve cytotoxic immunity and immunological memory as well as high levels of protective antibody. Genetic vaccines should serve as a safe alternative to the use of live vaccines and could be used in a variety of immunization protocols and in combination with other vaccines to achieve the desired results.

EXAMPLES

1. Preparation of Genetic Constructs for Use as Immunogens

The genetic sequences for Marburg Musoke and Ebola Zaire virus isolates have been fully determined, published, and are generally available in Genbank as described above. The Marburg Ravn glycoprotein sequence is presented herein.

Separate genetic vaccine expression vectors were constructed to include a glycoprotein-encoding fragment derived from the genomes of Marburg Musoke, Marburg Ravn or Ebola Zaire 95 virus. In each case, the glycoprotein-encoding chosen portions of the genome were those identified supra as preferred fragments. Each fragment, once transcribed, results in an mRNA that contains all of the sequences necessary to encode a filovirus glycoprotein of the type expressed in an infected cell during the pathogenic process initiated by the source filovirus. In these embodiments, the fragments were separately cloned into the BamHI cloning site on expression vector pWRG7077.

2. Introduction of Genetic Vaccine into Cells in Culture

To verify the ability of the genetic constructs to express the proper antigenic proteins in mammalian cells, in vitro tests were conducted on COS-7 cells (preferably 50–80% confluent) in culture. Quantities of the plasmids were produced using standard methods and were transfected using lipofectin, commercially available from Gibco-BRL, essentially as described by the producer.

Briefly, for each sample, 5 $\mu$g of DNA was added to 200 $\mu$l of OptiMEM medium. Forty $\mu$l of lipofectin brought to a volume of 200 $\mu$l using OptiMEM medium. Each mixture was incubated at room temperature for 30–45 minutes. The two were mixed together and incubated at room temperature for 10–15 minutes, then 1.6 ml of Optimem was added to bring the total volume to 2 ml. The COS-7 cells were washed once with 2 ml of serum-free medium then the 2 ml of the lipofectin/DNA mixture were added to the cells. The cells with lipofectin/DNA were incubated at 37° C. for 7 hours and then the medium was replaced with OptiMEM with Pen Strep Fungizone. The cells were then incubated from 26–27 after transfection in—cysteine and methionine media and were labeled from 27 to 30.5 hours with 200 $\mu$Ci $^{35}$S-Translabel (Amersham). The medium was removed and the cells were lysed by adding 0.5 ml of Triton X-100 lysis buffer (10 mM Tris-HCl, H 7.4, 1 mM EDTA, 0.25 M NaCl, 0.25 mg/ml each aprotinin and alpha-2-macroglobulin, 1t Triton X-100, 0.5% Sodium deoxycholate) with incubation on ice for 5 minutes. Four additional T25 flasks of COS cells were harvested in the same buffer for subsequent use to preadsorb antibodies.

The nuclei of the cells were spun out in a microfuge. The supernatants were transferred to clean microfuge tubes. Antibodies were added to the supernatants, which were then incubated overnight on ice. The antibodies for immunoprecipitation were obtained from serum of guinea pigs hyperimmunized with irradiated either an Ebola or a Marburg virus. To preadsorb the antibodies, the appropriate hyperimmune serum antibodies were mixed with 2 to 10 cell volumes (relative to the volume to be immunoprecipitated) and were incubated for 10 minutes or longer. Alternatively, monoclonal antibodies against Marburg and Ebola glycoproteins can be used and are available from the Centers for Disease Control in Atlanta, Ga.

One hundred $\mu$l of 50% Protein A Sepharose beads in the lysis buffer was added with shaking at 4° C. for 30 minutes, followed by brief centrifugation, then one wash in the lysis buffer, 2 washes in Triton X-100 wash buffer (10 mM Tris-HCl, H 7.4, 1 mM EDTA, 0.25 M NaCl, 1% Triton X-100, 0.5% Sodium deoxycholate) and 1 wash with 50 mM Tris pH 8.0.

The beads were resuspended in 30 $\mu$l of loading buffer and were boiled for 2 minutes before loading on a Laemmli protein gel.

Each sample from cells that received the glycoprotein constructs evidenced a protein of expected size. This confirmed the activity and expression of the plasmids in the COS cells, and also confirmed that the molecular weight forms of the antigens were similar to those produced in the normal host cells for the virus. Wide bands were observed in each test sample, which was believed to be due to extensive O-linked glycosylation of the glycoprotein.

3. Genetic Vaccination Protects Strain 13 Guinea Pigs from Death and Viremia After Challenge with Marburg Musoke Virus The plasmid encoding the Marburg Musoke glycoprotein was delivered into the skin of intact whole guinea pigs (Strain 13) using an accelerated-particle transfection protocol. Copies of the plasmid were coated onto gold carrier particles, as described in the prior example. The particles were deposited into sample cartridges and were then delivered into the guinea pigs. Bilateral abdominal delivery was performed after abdominal hair was clipped from the animal. In this and other genetic immunizations, 0.25 mg of gold particles (1–3μ, preferably 2–3μ) containing 2.0 μg of DNA per mg, were delivered to each target site on an animal. A typical immunization in guinea pigs involved delivery to four target sites, for a total of about 2 μg DNA per dose. Each delivery was made using a helium pulse apparatus at a helium pressure of about 350 to 400 psi.

Five Strain 13 guinea pigs each received a total of three vaccinations (about 2 μg DNA/vaccination), at four-week intervals. Four control animals were sham vaccinated using a plasmid that lacked the glycoprotein-encoding insert. Four weeks after the final vaccination, the test and control guinea pigs were challenged with a lethal dose of Marburg Musoke virus. All of the vaccinated animals remained healthy and non-viremic seven days after challenge. All of the control animals died.

The titer of antibodies directed against Marburg Musoke glycoprotein was determined by ELISA assay (calculated as the highest dilution of serum with $OD_{260}>0.2$) in test and control Strain 13 guinea pigs after each of three immunizations. Continuously increasing titers were observed in each test animal during the vaccination period. Control animals had no anti-gp titer. In all test animals, the maximal antibody titer was within 1 log of that observed in a positive control serum. In two of five animals, titers comparable to that of the positive control ($4 \log_{10}$) were observed.

4. Genetic Vaccination Protects Hartley Guinea Pigs from Death and Viremia After Challenge with Marburg Musoke or Marburq Ravn Virus The plasmid encoding either the Marburg Musoke glycoprotein or the Marburg Ravn glycoprotein was delivered into the skin of intact whole guinea pigs (Hartley) using the accelerated-particle transfection protocol described above.

Twelve Hartley guinea pigs in each set received a total of three vaccinations (about 2 μg DNA/vaccination) with either the Musoke-GP gene, the Ravn-GP gene, or both, at approximately four-week intervals. Eleven control animals were sham vaccinated using a plasmid that lacked the glycoprotein-encoding insert. Four weeks after the final vaccination, the test and control guinea pigs were challenged with a lethal dose of either Marburg Musoke or Marburg Ravn virus. The following table presents the results of those tests.

| GP Vaccine | Challenge Virus | Survivors | Sick | Viremic |
|---|---|---|---|---|
| Musoke | Musoke | 1/6 | 0/1 | 0/1 |
| Musoke | Ravn | 2/6 | 1/2 | 0/2 |
| Ravn | Musoke | 3/6 | 0/3 | 3/3 |
| Ravn | Ravn | 3/6 | 0/3 | 0/3 |
| Both | Musoke | 3/6 | 0/3 | 2/3 |
| Both | Ravn | 4/6 | 0/4 | 0/4 |
| Control | Musoke | 0/5 | | |
| Control | Ravn | 0/6 | | |

No simple correlation was observed between survival after challenge and the titer of antibodies against either Marburg Musoke or Marburg Ravn virus after immunization (FIGS. 3 and 4, respectively). Some, but not all, animals that survived virus challenge had high antibody titers (in the range of 2.5–3.5 $\log_{10}$). Some animals having high titers did not survive virus challenge. Some animals with modest titers (below 2.5 $\log_{10}$) did survive challenge. This was observed without regard to the strain of the immunogen Marburg glycoprotein(s) or of the challenge Marburg virus(es).

FIG. 5 shows the pre- and post-challenge ELISA titers of guinea pigs that survived challenge with a Marburg virus.

5. Genetic Vaccination Protects Strain 13 Guinea Pigs from Death After Challenge with Ebola Virus Five strain 13 guinea pigs were vaccinated three times at four week intervals as described herein. Six control guinea pigs were not vaccinated. The genetic vaccine employed in this test encoded the Ebola Zaire glycoprotein. After four weeks, the guinea pigs were challenged with Ebola Zaire virus. Three of the five vaccinated guinea pigs survived. One of the survivors was viremic, but recovered. The other two survivors were not viremic seven days after challenge. None of the control, unvaccinated guinea pigs survived. All guinea pigs developed ELISA titers of about 2.5 $\log_{10}$.

6. Genetic Vaccination Protects Balb/c Mice from Death and Viremia After Challenge with Ebola Virus Ebola virus (strain Zaire 95) was serially passaged in Balb/C mice until a virus was selected that could kill the mice after intraperitoneal injection. The selected virus was used to challenge vaccinated Balb/C mice in the following example.

Twenty Balb/C mice were vaccinated twice with the genetic construct encoding the Ebola glycoprotein, six weeks apart (2 targets per dose, 400 psi). Twenty additional Balb/C mice were vaccinated three times using the same genetic construct, four weeks apart. Certain doses were delivered with a modified instrument that necessitated a doubling of the amount of DNA delivered, but this did not appear to affect the results observed. Seventeen control mice were not immunized. All of the control mice died within about 1 week. No significant difference in survival was observed between the mice that received two vaccinations and those that received three (FIG. 6). In either case, between about 70 and 75% of the mice survived Ebola virus challenge. FIG. 7 depicts the ELISA titers of mice immunized twice with the Ebola glycoprotein construct. FIG. 8 depicts the ELISA titers of those mice immunized three times.

7. Immunization of Primates

Abdominal and thigh area hair of seven cynomologous monkeys was clipped and the skin was swabbed with ethanol. Vaccine doses (8 targets per monkey) containing 1.0 μg Marburg Musoke-GP (3 monkeys) or Ebola-GP (4 monkeys) constructs were delivered using the helium pulse apparatus at 450 psi. Delivery was unilateral, extending from the right inguinal node to the right hand sub-chest level abdominal skin.

Each monkey received a second immunization after about 10 weeks, using the same constructs as in the initial dose.

Positive ELISA antibody titers were observed in one monkey after the second vaccination dose. The monkeys will be challenged with the virus against which they have been immunized. It is anticipated that protection from viremia and death will be observed in challenged monkeys, since there is no indication that the disease process in primates or higher mammals is substantially different from that observed in mice or guinea pigs.

The present invention is not intended to be limited to the forgoing embodiments, but rather to encompass all such variations and modifications as come within the scope of the appended claims.

We claim:

1. A method of inducing an immune response to a Marburg or Ebola virus glycoprotein in a mammal, said method comprising:

(a) providing a genetic construction comprising a promoter operative in cells of the mammal and a coding region for a determinant of the glycoprotein, the genetic construction not comprising sequences necessary for replication of the virus;

(b) coating copies of the genetic construction onto carrier particles small in size in relation to the size of the cells of the mammal; and (c) accelerating the coated carrier particles into epidermal cells of the mammal in vivo, thereby inducing an immune response against the glycoprotein.

2. A method as claimed in claim 1 wherein the carrier particles are accelerated by a gaseous pulse in order to accelerate the carrier particles toward the mammal.

3. A method as claimed in claim 1 wherein the protein coding region encodes a glycoprotein selected from the group consisting of Ebola Zaire virus gp125, Marburg Musoke virus gp170, and Marburg Ravn virus glycoprotein.

4. A method as claimed in claim 1 wherein the protein coding region comprises SEQ ID NO: 1.

5. A method as claimed in claim 1 wherein the protein coding region comprises SEQ ID NO: 3.

6. A method as claimed in claim 1 wherein the protein coding region comprises SEQ ID NO: 5.

7. A composition of matter comprising a carrier particle and a genetic construction coated onto the carrier particle, wherein the genetic construction comprises a promoter operative in the cells of a mammal and a coding region for a determinant of a Marburg or Ebola virus glycoprotein.

8. A composition as claimed in claim 7 wherein the protein coding region encodes a glycoprotein selected from the group consisting of Ebola Zaire virus gp125, Marburg Musoke virus gp170, and Marburg Ravn virus glycoprotein.

9. A composition as claimed in claim 7 wherein the protein coding region comprises SEQ ID NO: 1.

10. A composition as claimed in claim 7 wherein the protein coding region comprises SEQ ID NO: 3.

11. A composition as claimed in claim 7 wherein the protein coding region comprises SEQ ID No. 5.

* * * * *